United States Patent [19]
Curiel et al.

[11] Patent Number: 5,910,486
[45] Date of Patent: Jun. 8, 1999

[54] METHODS FOR MODULATING PROTEIN FUNCTION IN CELLS USING, INTRACELLULAR ANTIBODY HOMOLOGUES

[75] Inventors: David T. Curiel; Jessy Deshane, both of Birmingham, Ala.

[73] Assignee: UAB Research Foundation, Birmingham, Ala.

[21] Appl. No.: 08/468,252

[22] Filed: Jun. 6, 1995

Related U.S. Application Data

[63] Continuation of application No. 08/301,339, Sep. 6, 1994, abandoned.
[51] Int. Cl.$^6$ ...................................................... A61K 48/00
[52] U.S. Cl. ................................................................ 514/44
[58] Field of Search ............................. 435/172.3; 514/44

[56] References Cited

FOREIGN PATENT DOCUMENTS 9402610  2/1994  WIPO.

OTHER PUBLICATIONS

Adams, G.P. et al., "Highly Specific in Vivo Tumor Targeting by Monovalent and Divalent Forms of 741F8 Anti--c-erbB-2 Single Chain Fv" *Cancer Research*, vol. 53, pp. 4026–4034, Sep. 1, 1993.

Batra, J.K. et al., "Recombinant anti-erbB2 immunotoxins containing Pseudomonas exotoxin" *Proc. Natl. Acad. Sci. USA*, vol. 89, pp. 5867–5871, Jul. 1992.

Biocca, S. et al., "Intracellular Expression of Anti-p21$^{ras}$ Single chain Fv Fragments Inhibits Meiotic Maturation of Xenopus Oocytes" *Biochemical and Biophysical Research Communications*, vol. 197, No. 2, pp. 422–427, Dec. 15, 1993.

Biocca, S. et al., "Intracellular Immunization with Cytosolic Recombinant Antibodies" *Bio/Technology*, vol. 12, pp. 396–399, Apr. 1994.

Carlson, J.R., "A New Means of Inducibly Inactivating a Cellular Protein" *Molecular and Cellular Biology*, vol. 8, No. 6, pp. 2638–2646, Jun. 1988.

Carter, P., et al., "Humanization of an anti-p185$^{HER2}$ antibody for human cancer therapy" *Proc. Natl. Acad. Sci. USA*, vol. 89, pp. 4285–4289, May 1992.

DeSantes, K. et al., "Radiolabeled Antibody Targeting of the HER-2/neu Oncoprotein" *Cancer Research*, vol. 52, pp. 1916–1923, Apr. 1, 1992.

Drebin, J.A. et al., "Monoclonal antibodies specific for the neu oncogene product directly mediate anti-tumor effects in vivo" *Oncogene*, vol. 2, pp. 387–394, 1988.

Fendly, B.M. et al., "Characterization of Murine Monoclonal Antibodies Reactive of Either the Human Epidermal Growth Factor Receptor or HER2/neu Gene Product" *Cancer Research*, vol. 50, pp. 1550–1558, Mar. 1, 1990.

Hiatt, A. et al., "Production of antibodies in trangenic plants" *Nature*, vol. 342, pp. 76–78, Nov. 2, 1989.

Hudziak, R.M. et al., "Increased expression of the putative growth factor receptor p185$^{HER2}$ causes transformation and tumorigenesis of NIH 3T3 cells" *Proc. Natl. Acad. Sci. USA*, vol. 84, pp. 7159–7163, Oct. 1987.

Marasco, W.A. et al., "Design, intracellular expression, and activity of a human anti-human immunodeficiency virus type 1 gp120 single-chain antibody" *Proc. Natl. Acad. Sci. USA*, vol. 90, pp. 7889–7893, Aug. 1993.

Moritz, D. et al, "Cytotoxic T lymphocytes with a grafted recognition specificity for ERBB2-expressing tumor cells" *Proc. Natl. Acad. Sci. USA*, vol. 91, pp. 4318–4322, May 1994.

Muller, W.J. et al., "Single-Step Induction of Mammary Adenocarcinoma in Transgenic Mice Bearing the Activated c-neu Oncogene" *Cell*, vol 54, pp. 105–115, Jul. 1, 1988.

Stancovski, I. et al, "Targeting of T Lymphocyts to Neu/HER2-Expressing Cells Using Chimeric Single Chain Fv Receptors" *Journal of Immunology*, vol. 151, No. 11, pp. 6577–6582, Dec. 1, 1993.

Wels W. et al., "Construction, Bacterial Expression and Characterization of a Bifunctional Single-Chain Antibody-Phosphatase Fusion Protein Targeted to the Human ERBB2-Receptor" *Biotechnology*, vol. 10, pp. 1128–1132, 1992.

Wels, W. et al., "Diminution of Antibodies Directed Against Tumor Cell Surface Epitopes: A Single Chain Fv Fusion Molecule Specifically Recognized the Extracellular Domain of the c-erb B-2 Receptor" *J. Steroid Biochem. Molec. Biol.*, vol. 43, No. 1–3, pp. 1–7, 1992.

Wels, W. et al., "Selective Inhibition of Tumor Cell Growth by a Recombinant Single-Chain Antibody-Toxin Specific for the erbB-2 Receptor" *Cancer Research*, vol. 52, pp. 6310–6317, Nov. 15, 1992.

Werge, T.M. et al., "Intracellular immunization: Cloning and intracellular expression of a monoclonal antibody to the p21$^{ras}$" *FEBS*, vol. 274, No. 1,2, pp. 193–198, Nov. 1990.

Winter, G. and C. Milstein, "Man-made antibodies" *Nature*, vol. 349, pp. 293–299, Jan. 24, 1991.

Brocea et al BBRC 197(2) 422, 1993, Jun. 1997.

(List continued on next page.)

*Primary Examiner*—Bruce R. Campell
*Attorney, Agent, or Firm*—Benjamin Aaron Adler

[57] ABSTRACT

Methods and compositions for modulating protein function in a cell involving intracellular expression of an antibody homologue that binds to the protein within the cell are disclosed. In a preferred embodiment, an antibody homologue, such as a single chain Fv (sFv) fragment, is expressed within an intracellular compartment of a cell, such as the endoplasmic reticulum (ER), to inhibit cell surface expression of a membrane protein. Preferably, the cell is a malignant mammalian cell and the protein is a cell surface receptor oncoprotein, such as c-erbB2. Intracellular binding of the antibody homologue to the receptor oncoprotein inhibits its surface expression and, moreover, inhibits cell proliferation and cell survival. Isolated nucleic acid molecules encoding anti-c-erbB2 antibody homologues, as well as recombinant expression vectors and host cells incorporating these nucleic acid molecules, are also disclosed.

20 Claims, 11 Drawing Sheets

OTHER PUBLICATIONS

Orkin et al. Dec. 1995, Jun. 1997.
Caufen et al New Scientist, Nov. 25, 1995, Jun. 1997.
Marshal et al Science 269:1050, 1995, Jun. 1997.
Werge et al FEBS 274 (1,2): 193, 1990, Jun. 7, 1997.
Wels et al Cancer Res. 52: 6310, 1992, Jun. 7, 1997.
Marasco et al PNAS 90: 7889, 1993, Jun. 7, 1997.
Wels et al J. Steroid Biochem Mol. Biol 43(1–3): Jan. 1992, Jun. 7, 1997.

J Deshane et al. (1994) Gene Therapy 1: 332–337.

IM Harwerth et al (1993) British J Cancer 68: 1140–1145.

JA Drebin et al (1986) Proc Natl Acad SCi USA 83: 9129–9133.

JG Altin et al (1991) Growth Factors 4: 145–155 (Abstract only).

JR Starkey et al. (1991) FASEB J 5: A1259.

R Hesketh (1995) The Oncogene Facts Book pp. 32–42.

5,910,486

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:1:

```
AGGGTACCAT GGACGTCCAG CTGACC                                    26
```

(2) INFORMATION FOR SEQ ID NO:2:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:2:

```
GCTCTAGATT AGGAGACGGT GACCGTGGTC C                              31
```

(2) INFORMATION FOR SEQ ID NO:3:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:3:

```
Met Lys Ser His Ser Gln Val Phe Val Phe Leu Leu Leu Cys Val Ser
 1               5                  10                  15

Gly Ala His Gly
            20
```

(2) INFORMATION FOR SEQ ID NO:4:

(i) SEQUENCE CHARACTERISTICS:
        (A) LENGTH: 711 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..711

(xi) SEQUENCE DESCRIPTION: SEQ ID NO:4:

```
ATG GAC CTG CAG CTG ACC CAG TCT CCA GCA ATC CTC TCT GCA TCT CCA      48
Met Asp Leu Gln Leu Thr Gln Ser Pro Ala Ile Leu Ser Ala Ser Pro
 1               5                  10                  15

GGG GAG AAG GTC ACA ATG ACT TGC AGG GCC ACC CCA AGT GTA AGT TAC      96
Gly Glu Lys Val Thr Met Thr Cys Arg Ala Thr Pro Ser Val Ser Tyr
            20                  25                  30

ATG CAC TGG TAT CAG CAG AAG CCA GGA TCC TCC CCC AAA CCT TGG ATT     144
Met His Trp Tyr Gln Gln Lys Pro Gly Ser Ser Pro Lys Pro Trp Ile
        35                  40                  45

TAT ACC ACA TCC AAC CTG GCT TCT GGA GTC CCT GCT CGC TTC AGT GGC     192
Tyr Thr Thr Ser Asn Leu Ala Ser Gly Val Pro Ala Arg Phe Ser Gly
    50                  55                  60
```

```
GGT GGG TCT GGG ACC TCT TAC TCT CTC ACA GTC AGC AGA GTG GAG GCT      240
Gly Gly Ser Gly Thr Ser Tyr Ser Leu Thr Val Ser Arg Val Glu Ala
 65                  70                  75                  80

GAA GAT GCT GCC ACT TAT TAC TGC CAG CAG TGG AGT CGT AGC CCA CCC      288
Glu Asp Ala Ala Thr Tyr Tyr Cys Gln Gln Trp Ser Arg Ser Pro Pro
                     85                  90                  95

ACG TTC GGA GGG GGG TCC AAG CTG GAA ATA AAA GGT TCT ACC TCT GGT      336
Thr Phe Gly Gly Gly Ser Lys Leu Glu Ile Lys Gly Ser Thr Ser Gly
                100                 105                 110

TCT GGT AAA TCT TCT GAA GGT AAA GGT GTG CAG CTG CAG GAG TCA GGA      384
Ser Gly Lys Ser Ser Glu Gly Lys Gly Val Gln Leu Gln Glu Ser Gly
            115                 120                 125

CCT GAG GTG GTC AAG CCT GGA GGT TCA ATG AAG ATA TCC TGC AAG ACT      432
Pro Glu Val Val Lys Pro Gly Gly Ser Met Lys Ile Ser Cys Lys Thr
        130                 135                 140

TCT GGT TAC TCA TTC ACT GGC CAC ACC ATG AAC TGG GTG AAG CAG AGC      480
Ser Gly Tyr Ser Phe Thr Gly His Thr Met Asn Trp Val Lys Gln Ser
145                 150                 155                 160

CAT GGA AAG AAC CTT GAG TGG ATT GGA CTT ATT AAT CCT TAC AAT GGT      528
His Gly Lys Asn Leu Glu Trp Ile Gly Leu Ile Asn Pro Tyr Asn Gly
                165                 170                 175

GAT ACT AAC TAC AAC CAG AAG TTC AAG GGC AAG GCC ACA TTT ACT GTA      576
Asp Thr Asn Tyr Asn Gln Lys Phe Lys Gly Lys Ala Thr Phe Thr Val
            180                 185                 190

GAC AAG TCG TCC AGC ACA GCC TAC ATG GAG CTC CTC AGT CTG ACA TCT      624
Asp Lys Ser Ser Ser Thr Ala Tyr Met Glu Leu Leu Ser Leu Thr Ser
        195                 200                 205

GAG GAC TCT GCA GTC TAT TAC TGT GCA AGG AGG GTT ACG GAC TGG TAC      672
Glu Asp Ser Ala Val Tyr Tyr Cys Ala Arg Arg Val Thr Asp Trp Tyr
210                 215                 220

TTC GAT GTC TGG GGG GCA GGG ACC ACG GTC ACC GTC TCC                  711
Phe Asp Val Trp Gly Ala Gly Thr Thr Val Thr Val Ser
225                 230                 235

(2) INFORMATION FOR SEQ ID NO:5:

(i) SEQUENCE CHARACTERISTICS:
        (A) LENGTH: 237 amino acids
        (B) TYPE: amino acid
        (D) TOPOLOGY: linear (ii) MOLECULE TYPE: protein (xi) SEQUENCE DESCRIPTION: SEQ ID NO:5:

Met Asp Leu Gln Leu Thr Gln Ser Pro Ala Ile Leu Ser Ala Ser Pro
 1               5                  10                  15

Gly Gln Lys Val Thr Met Thr Cys Arg Ala Thr Pro Ser Leu Ser Tyr
                20                  25                  30

Met His Trp Tyr Gln Gln Lys Pro Gly Ser Ser Pro Lys Pro Trp Ile
            35                  40                  45

Tyr Thr Thr Ser Asn Leu Ala Ser Gly Val Pro Ala Arg Phe Ser Gly
        50                  55                  60

Gly Gly Ser Gly Thr Ser Tyr Ser Leu Thr Val Ser Arg Val Glu Ala
 65                 70                  75                  80

Glu Asp Ala Ala Thr Tyr Tyr Cys Gln Gln Trp Ser Arg Thr Pro Pro
                85                  90                  95

Thr Phe Gly Gly Gly Ser Lys Leu Glu Ile Lys Arg Ser Thr Ser Gly
               100                 105                 110

Ser Gly Lys Ser Ser Glu Gly Lys Gly Val His Leu Gln Glu Ser Gly
           115                 120                 125
```

```
Pro Asp Val Val Lys Pro Gly Gly Ser Met Lys Ile Ser Cys Lys Thr
    130             135             140

Ser Gly Tyr Ser Phe Thr Gly His Thr Met Asn Ser Val Lys Gln Thr
145             150             155             160

His Gly Lys Asn Leu Glu Trp Ile Ala Leu Ile Asn Pro Tyr Asn Gly
                165             170             175

Asp Thr Asn Tyr Asn Gln Lys Phe Lys Gly Lys Ala Thr Phe Thr Val
            180             185             190

Asp Lys Ser Ser Ser Thr Ala Tyr Met Glu Leu Leu Ser Leu Thr Ser
        195             200             205

Glu Asp Ser Ala Val Tyr Tyr Cys Ala Arg Arg Val Thr Asp Trp Tyr
    210             215             220

Phe Asp Val Trp Pro Ala Gly Thr Thr Val Thr Val Ser
225             230             235
```

METHODS FOR MODULATING PROTEIN FUNCTION IN CELLS USING, INTRACELLULAR ANTIBODY HOMOLOGUES

REFERENCE TO RELATED APPLICATION

This is a continuation application of U.S. patent application Ser. No. 08/301,339, filed Sep. 6, 1994, abandoned.

BACKGROUND OF THE INVENTION

ErbB2 is a 185-kDa transmembrane protein kinase receptor with extensive homology to the family of epithelial growth factor receptors (for a review, see Yarden Y., and Ullrich, A. (1988) *Ann. Rev. Biochem.* 57:443–478). Several lines of evidence suggest that aberrant expression of the erbB2 gene may play an important role in neoplastic transformation and progression. In this regard, ectopic expression of erbB2 has been shown to be capable of transforming rodent fibroblasts in vitro (Hudziak, R. M., et al. (1987) *Proc. Natl. Acad. Sci. USA* 84:7159–7163). In addition, transgenic mice carrying either normal or mutant erbB2 develop a variety of tumors, predominantly including neoplasms of mammary origin (Muller, W. J., et al. (1988) *Cell* 54:105–115). Importantly, it has been shown that amplification and/or over-expression of the erbB2 gene occurs in a variety of human epithelial carcinomas, including malignancies of the breast, ovary, gastro-intestinal tract, salivary gland, and lung (Slamon, D. J., et al. (1989) *Science* 707–712; Semba, K., et al. (1985) *Proc. Natl. Acad. Sci. USA* 82;6497–6501; Fukushige, S. I., et al. (1986) *Mol. Cell. Biol.* 6:955–958). In the instances of breast and ovarian carcinoma, a direct correlation has been noted between over-expression of erbB2 and aggressive tumor growth with reduced overall patient survival (Hynes, N. E. (1993) *Cancer Biology* 4:19–26; Gerdes, J., et al. (1984) *J. Immunol.* 133:1710–1715). There is a lack of effective therapy for erbB2 overexpressing tumors which, in many cases, do not respond well to chemotherapy.

The association of over-expression of the erbB2 gene product with poor clinical prognosis has led to the development of therapeutic strategies to target tumor cells exhibiting increased surface levels of erbB2. Towards this end, monoclonal antibodies (mAbs) have been developed which exhibit high affinity binding to the extracellular domains of the erbB2 protein (Fendly, B. M., et al. (1990) *Cancer Research* 50:1550–1558; Drebin, J. A., et al. (1988) *Oncogene* 2:387–394). A number of studies have demonstrated that a subset of these mAbs can elicit growth inhibition of erbB2 over-expressing tumor cells both in vitro and in vivo (Drebin, J. A., et al. (1988) *Oncogene* 2:387–394). Based upon these observations, clinical trials in humans have been undertaken which exploit the direct antiproliferative effect of anti-erbB2 mAbs (Carter, P., et al. (1992) *Proc. Natl. Acad. Sci. USA* 89:4285–4289). The utility of antibody based tumor targeting has also been proposed in the context of radiolabeled anti-erbB2 mAbs (DeSantes, K., et al. (1992) *Cancer Research* 52:1916–1923). In addition, antitumor therapies directed at erbB2 have been developed utilizing targeted immunotoxins (Batra, J. K., et al. (1992) *Proc. Natl. Acad. Sci. USA* 89:5867–5871). These experimental strategies have employed recombinant fusion proteins consisting of various bacterial toxins selectively targeted to tumor cells by virtue of single-chain anti-erbB2 antibody (sFv) moieties.

Alternative to the therapeutic strategies described above that target an antibody to erbB2 expressed on the surface of tumor cells, a number of anti-cancer gene therapy strategies have been developed which employ various methods of molecular ablation of inappropriately or overexpressed genes to revert the transformed phenotype. These strategies have included antisense nucleic acid-mediated inhibition directed at the transcriptional or translational level of gene expression in the context of dominant oncogenes (Ebbinghaus, S. W., et al. (1993) *J Clin. Invest.* 92:2433–2439) and transdominant mutations to achieve functional inactivation of over-expressed growth factor receptors (Kashles, O., et al. (1991) *Mol. Cell. Biol.* 11:1454–1463).

Accordingly, given the overexpression of erbB2 in many forms of human cancers, manipulation of the expression and/or function of erbB2 in tumor cells may be beneficial therapeutically. Additional methods for interfering with the expression and/or function of erbB2, as well as other oncoproteins, in tumor cells are still needed.

SUMMARY OF THE INVENTION

This invention pertains to methods and compositions for modulating protein function in a cell involving intracellular expression of an antibody homologue that binds to the protein within the cell, thereby altering the function of the protein. The invention is particularly applicable to inhibiting the surface expression of erbB2 on a malignant cell, to thereby inhibit proliferation and survival of the cell, although the methods of the invention can be similarly used to inhibit the function of other proteins. In contrast to other approaches for inhibiting erbB2 function which target cell-surface erbB2 (e.g., radiolabeled antibodies or immunotoxins) or the erbB2 gene or mRNA (e.g., antisense nucleic acid), the methods of the invention are based upon targeting of an immature intracellular form of erbB2. As demonstrated herein, disruption of surface expression of erbB2 by intracellular antibody ablation in malignant cells that overexpress erbB2 inhibits both cell proliferation and cell survival. Accordingly, the invention provides an alternative therapeutic approach for modulating oncoprotein function, and in particular erbB2 function.

To alter the function of erbB2 or other protein according to the invention, an antibody homologue specific for the protein is expressed intracellularly. To express an antibody homologue within a cell, a nucleic acid molecule encoding the antibody homologue, such as a recombinant expression vector encoding the antibody homologue, is introduced into the cell. Preferably, the antibody homologue used to modulate protein function is a single chain Fv (sFv) fragment, although whole antibodies, or antigen binding fragments thereof (e.g., Fab fragments) may also be useful.

In a preferred embodiment of the invention, the antibody homologue is expressed within an intracellular compartment of a cell. In a particularly preferred embodiment, the antibody homologue is expressed in the endoplasmic reticulum (ER) to inhibit cell surface expression of a membrane protein (e.g., erbB2) as a result of binding of the antibody homologue to an immature form of the protein within the ER. Similarly, secretion of a soluble protein from a cell can be inhibited by expression of an antibody homologue within the ER of the cell. Targeting of an antibody homologue to an intracellular compartment such as the ER can be accomplished by incorporating an appropriate signal sequence into the antibody homologue.

In a particularly preferred embodiment of the invention, an antibody homologue is expressed intracellularly in a malignant mammalian cell to inhibit the function of an oncoprotein. Preferably, the oncoprotein is normally expressed on the cell surface and functions as a receptor (e.g., a receptor tyrosine kinase). A particularly preferred cell surface receptor oncoprotein to be inhibited is erbB2. Intracellular binding of the antibody homologue to the receptor oncoprotein inhibits its surface expression and, moreover, inhibits cell proliferation and cell survival. A nucleic acid molecule encoding an antibody homologue in a form that is expressed within the endoplasmic reticulum can be introduced into erbB2 overexpressing malignant cells, including epithelial carcinoma cells from such tissues and organs as breast, ovary, gastrointestinal tract, lung and salivary gland. A nucleic acid molecule encoding the antibody homologue can be introduced into malignant cells in vivo by, for example, use of a recombinant viral vector or other vector system suitable for delivery of genes to cells in vivo.

Another aspect of the invention pertains to an isolated nucleic acid molecule encoding an anti-erbB2 antibody homologue in a form that is expressed in a mammalian cell in an intracellular compartment, such as the ER. In one embodiment, the nucleic acid comprises a first nucleotide sequence encoding a signal sequence operatively linked in a 5' to 3' direction by a phosphodiester bond to a second nucleotide sequence encoding a single chain Fv fragment that binds a human erbB2 oncoprotein. The signal sequence encoded by the first nucleotide sequence directs expression of a protein which contains the signal sequence to an endoplasmic reticulum. The isolated nucleic acids of the invention can be incorporated into recombinant expression vectors, such as plasmid or viral vectors, to facilitate expression of the antibody homologue within a cell. Host cells, such as an epithelial carcinoma cell into which a recombinant expression vector of the invention has been introduced, are also described.

DETAILED DESCRIPTION OF THE INVENTION

Figure 1:
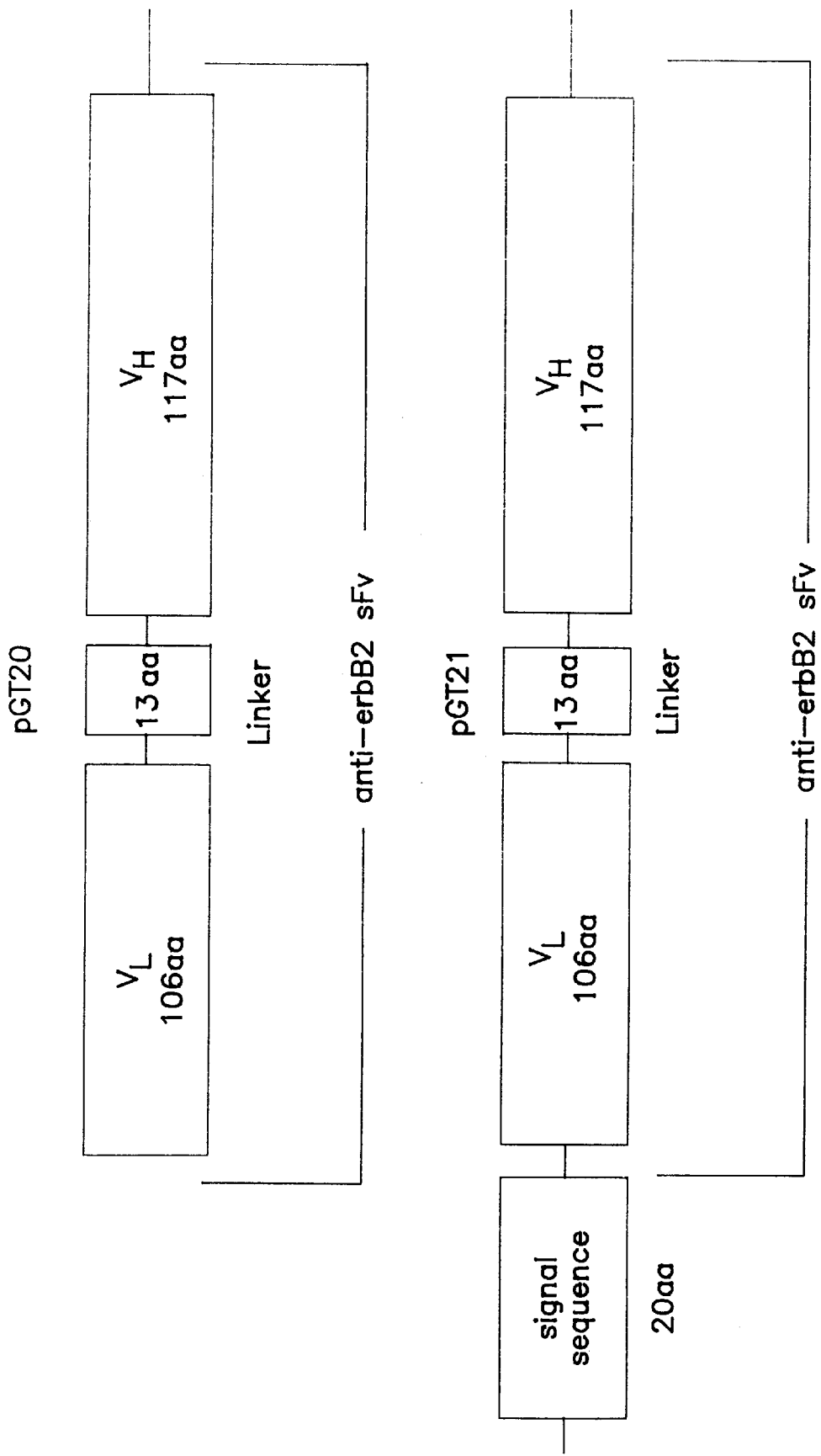
FIG. 1 is a schematic representation of the anti-erbB2 single chain antibody (sFv) gene constructs present in the pGT20 and pGT21 expression vectors.

This invention pertains to methods and compositions for modulating protein function in a cell involving intracellular expression of an antibody homologue that binds to the protein within the cell, thereby altering the function of the protein. The invention is described herein with regard in particular to inhibition of the expression of the erbB2 oncoprotein on the surface of erbB2 overexpressing tumor cells. However, the invention can be applied to modulating the function of other proteins as well. Various aspects of the invention are described in further detail in the following subsections:

A. Antibody Homologues

To inhibit the expression and/or function of a cellular protein according to the invention, an antibody homologue specific for the protein is expressed intracellularly such that the antibody homologue binds to the protein intracellularly, thereby inhibiting the protein's expression (e.g., on the cell surface) and/or function. A particularly preferred antibody homologue for use in the invention is a single chain Fv fragment (also referred to herein as a single chain antibody).

The term "antibody homologue" as used herein refers to whole immunoglobulin molecules, immunologically active portions or fragments thereof and recombinant forms of immunoglobulin molecules, or fragments thereof, that contain an antigen binding site which specifically binds (immunoreacts with) an antigen (e.g., cellular protein). Additionally, the term antibody homologue is intended to encompass non-antibody molecules that mimic the antigen binding specificity of a particular antibody. Such agents are referred to herein as "antibody mimetic agents".

The term "antibody combining site", as used herein refers to that structural portion of an antibody molecule comprised of a heavy and light chain variable and hypervariable regions that specifically binds (immunoreacts with) antigen.

The terms "bind", "immunoreact" or "reactive with" in its various forms is used herein to refer to an interaction between an antigenic determinant-containing molecule (i.e., antigen) and a molecule containing an antibody combining site, such as a whole antibody molecule or a portion thereof, or recombinant antibody molecule (i.e., antibody homologue).

The term "monoclonal antibody" or "monoclonal antibody composition", as used herein, refers to a population of antibody molecules that contain only one species of an antigen binding site capable of immunoreacting with a particular epitope of an antigen. A monoclonal antibody composition thus typically displays a single binding affinity for a particular antigen with which it immunoreacts.

The term "immunogen" is used herein to describe a composition typically containing a peptide or protein as an active ingredient (i.e., antigen) used for the preparation of antibodies against the peptide or protein. Alternatively, the immunogen can be a nucleic acid (e.g., DNA) in a form suitable for expression of an encoded protein or peptide by cells upon introduction of the nucleic acid into the cells, with the expressed protein or peptide thereby acting as an antigen to stimulate an antibody response (so-called "intracellular immunization").

Structurally, the simplest naturally occurring antibody (e.g., IgG) comprises four polypeptide chains, two heavy (H) chains and two light (L) chains inter-connected by disulfide bonds. It has been shown that the antigen-binding function of an antibody can be performed by fragments of a naturally-occurring antibody. Thus, these antigen-binding fragments are intended to be encompassed by the term "antibody homologue". Examples of binding fragments include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment, which consists of a VH domain; (v) an isolated complimentarity determining region (CDR); and (vi) an F(ab')$_2$ fragment, a bivalent fragment comprising two Fab fragments linked by a disulfide bridge at the hinge region.

Furthermore, although the two domains of the Fv fragment are coded for by separate genes, a synthetic linker can be made that enables them to be made as a single chain protein (referred to herein as single chain antibody or a single chain Fv (sFv); see e.g., Bird et al. (1988) *Science* 242:423–426; and Huston et al. (1988) *Proc. Natl. Acad. Sci. USA* 85:5879–5883). Such single chain antibodies are also encompassed within the term "antibody homologue". Other forms of recombinant antibodies, such as chimeric, humanized and bispecific antibodies are also within the scope of the invention.

B. Isolation of Antibody Genes

To express an antibody homologue within a cell, a nucleic acid molecule(s) encoding the antibody homologue is prepared and introduced into the cell. An isolated nucleic acid molecule encoding an antibody homologue can be prepared according to standard molecular biology methods using nucleic acid sequences obtained from antibody genes. Isolated nucleic acid molecules encoding antibody chains (or relevant antigen binding portions thereof, such as VH or VL regions), specific for many different particular proteins have been described, and/or are available, in the art. Additionally, such nucleic acids can be isolated by standard techniques, for example, from a hybridoma that expresses a monoclonal antibody specific for a protein of interest or by screening an immunoglobulin expression library (e.g., an immunoglobulin phage display library) with a protein of interest.

1. From Hybridomas

A hybridoma secreting a monoclonal antibody specific for a particular antigen is typically prepared by first immunizing a suitable subject with an appropriate immunogenic preparation of the antigen. The unit dose of immunogenic preparation and the immunization regimen will depend upon the species of mammal immunized, its immune status, the body weight of the mammal and the antigen concentration of the immunogenic preparation administered. For immunization, the immunogenic preparation is typically administered with an adjuvant, such as Freund's complete or incomplete adjuvant.

After a polyclonal antibody response against the antigen has been stimulated in the subject, antibody-producing cells (i.e., B lymphocytes) are recovered from the subject, fused with an immortalized cell line and the resultant hybridomas screened for production of a monoclonal antibody that binds the antigen (e.g., by an enzyme-linked immunosorbent assay (ELISA), radioimmunoassay, flow cytometry or other suitable assay). The technology for producing monoclonal antibody hybridomas is well known (see generally R. H. Kenneth, in *Monoclonal Antibodies: A New Dimension In Biological Analyses,* Plenum Publishing Corp., New York, N.Y. (1980); E. A. Lerner (1981) *Yale J Biol. Med,* 54:387–402; M. L. Gefter et al. (1977) *Somatic Cell Genet.,* 3:231–36).

Any suitable technique for preparing hybridomas can be used including, but are not limited to, the hybridoma technique originally described by Kohler and Milstein (1975, *Nature* 256:495–497) (see also, Brown et al. (1981) *J. Immunol* 127:539–46; Brown et al. (1980) *J. Biol Chem* 255:4980–83; Yeh et al. (1976) *Proc. Natl. Acad. Sci. USA* 76:2927–31; and Yeh et al. (1982) *Int. J Cancer* 29:269–75), and the more recent human B cell hybridoma technique (Kozbor et al. (1983) *Immunol Today* 4:72), EBV-hybridoma technique (Cole et al. (1985), *Monoclonal Antibodies and Cancer Therapy,* Alan R. Liss, Inc., pp. 77–96) and trioma techniques. Moreover, the ordinary skilled worker will appreciate that there are many variations of such methods which also would be useful.

Typically, the immortal cell line (e.g., a myeloma cell line) is derived from the same mammalian species as the lymphocytes. For example, murine hybridomas can be made by fusing lymphocytes from a mouse immunized with an immunogenic preparation of a protein of interest with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3x63-Ag8.653 or Sp2 2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed).

Once a hybridoma specific for a protein of interest is prepared, nucleic acid encoding the antibody chains (or relevant antigen binding portion thereof) expressed by the hybridoma can be isolated by standard techniques. For example cDNA can be prepared from mRNA obtained from the hybridoma and DNA encoding the antibody chain, or portion thereof, can be amplified by the polymerase chain reaction (PCR) to isolate DNA encoding an antibody chain. Alternatively, the cDNA (e.g., in a cDNA library) can be screened with an appropriate probe specific for antibody genes to isolate DNA encoding an antibody chain. The nucleic acid so isolated can be further manipulated (e.g., linked to other nucleic acid sequences) and subcloned into expression vectors using standard recombinant DNA techniques, as described in further detail below.

2. From Recombinant Immunoglobulin Libraries

Alternatively, monoclonal antibodies can be prepared by constructing a recombinant immunoglobulin library, such as a sFv or Fab phage display library and nucleic acid encoding an antibody chain (or portion thereof) can be isolated therefrom. Immunoglobulin light chain and heavy chain first strand cDNAs can be prepared from mRNA derived from lymphocytes of a subject immunized with a protein of interest using primers specific for a constant region of the heavy chain and the constant region of each of the κ and λ light chains. Using primers specific for the variable and constant regions, the heavy and light chain cDNAs can then by amplified by PCR. The amplified DNA is then ligated into appropriate vectors for further manipulation in generating a library of display packages. Restriction endonuclease recognition sequences may also be incorporated into the primers to allow for the cloning of the amplified fragment into a vector in a predetermined reading frame for expression on the surface of the display package.

The immunoglobulin library is expressed by a population of display packages, preferably derived from filamentous phage, to form an antibody display library. In addition to commercially available kits for generating phage display libraries (e.g., the Pharmacia Recombinant Phage Antibody System, Catalog No. 27-9400-01; and the Stratagene SurfZAP™ Phage Display Kit, Catalog No. 240612), examples of methods and reagents particularly amenable for use in generating antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J Mol Biol* 226:889–896; Clackson et al. (1991) *Nature* 352:624–628; Gram et al. (1992) *Proc. Natl. Acad. Sci. USA* 89:3576–3580; Garrad et al. (1991) *Bio/Technology* 2:1373–1377; Hoogenboom et al. (1991) *Nuc Acid Res* 19:4133–4137; and Barbas et al. (1991) *Proc. Natl. Acad. Sci. USA* 88:7978–7982. As generally described in McCafferty et al. *Nature* (1990) 348:552–554, complete VH and VL domains of an antibody, joined by a flexible $(Gly_4-Ser)_3$ linker, can be used to produce a single chain antibody expressed on the surface of a display package, such as a filamentous phage.

Once displayed on the surface of a display package (e.g., filamentous phage), the antibody library is screened with a protein of interest to identify and isolate packages that express an antibody that binds the protein of interest. Display packages expressing antibodies that bind immobilized protein can then be selected. Following screening and identification of a monoclonal antibody (e.g., a monoclonal sFv) specific for the protein of interest, nucleic acid encoding the selected antibody can be recovered from the display package (e.g., from the phage genome) by standard techniques. The nucleic acid so isolated can be further manipulated if desired (e.g., linked to other nucleic acid sequences) and subcloned into other expression vectors by standard recombinant DNA techniques, as described in further detail below.

C. Manipulation of Antibody Genes

Once isolated, nucleic acid molecules encoding antibody chains, or portions thereof, can be further manipulated using standard recombinant DNA techniques. For example, a single chain antibody gene can be created by linked a VL coding region to a VH coding region via a nucleotide sequence encoding a flexible linker (e.g., $(Gly_4-Ser)_3$). Single chain antibodies can be engineered in accordance with the teachings of Bird et al. (1988) *Science* 242:423–426; Huston et al. (1988) *Proc. Natl. Acad. Sci USA* 85:5879–5883; Ladner, et al. International Publication Number WO 88/06630; and McCafferty, et al. International Publication No. WO 92/10147. A preferred single chain antibody for use in the invention binds to the human erbB2 oncoprotein (referred to herein as an anti-erbB2 sFv). A plasmid (e23scFv) encoding an anti-erbB2 sFv immunotoxin is described in Batra, J. K., et al. (1992) *Proc. Natl. Acad. Sci. USA* 89:5867–5871. The anti-erbB2 sFv portion of this construct can be obtained by PCR using the e23scFv plasmid as the template and oligonucleotide primers shown in SEQ ID NO: 1 and 2, as described in Example 1. The nucleotide and amino acid sequences of the anti-erbB2 sFv is shown in SEQ ID NO: 4 and 5, respectively. The anti-erbB2 sFv coding region can be linked to other sequences, e.g., sequences that direct expression of the sFv to a particular cellular location, as described further below.

Another manipulation that can be performed on isolated antibody genes is to link the antibody gene to a nucleotide sequence encoding an amino acid sequence that directs the antibody homologue to a particular intracellular compartment. A preferred nucleotide sequence to which an antibody gene is linked encodes a signal sequence (also referred to as a leader peptide). Signal sequences are art-recognized amino acid sequences that direct a protein containing the signal sequence at its amino-terminal end to the endoplasmic reticulum (ER). Typically, signal sequences comprise a number hydrophobic amino acid residues. An example of a suitable signal sequence which can be linked to an antibody homologue to direct it to the ER is shown in SEQ ID NO: 3; although other suitable signal sequences can also be used. A nucleotide sequence encoding a signal sequence can be linked to an antibody gene by standard PCR techniques.

Alternatively, an antibody homologue can be linked to an amino acid sequence that directs the antibody homologue to a different compartment of the cell. For example, a nuclear localization sequence (NLS) can be linked to the antibody homologue to direct the antibody homologue to the cell nucleus. Nuclear localization sequences are art-recognized targeting sequences. Typically, an NLS is composed of a number of basic amino acid residues.

Yet another possible manipulation of antibody genes is to engineer chimeric and humanized antibody derivatives. Chimeric and humanized antibodies, which combine regions of animal and human antibodies, retain the antigenic binding specificity of the original monoclonal antibody, but may be less immunogenic than entirely animal-derived antibodies when used in humans. The terms "chimeric antibody" as used herein refers to an antibody molecules that combines a non-human animal variable region and a human constant region. To create a chimeric antibody gene, a gene encoding the constant region of a non-human antibody molecule is substituted with a gene encoding a human constant region. (see Robinson et al. International Patent Publication PCT/US86/02269; Akira, et al. European Patent Application 184,187; Taniguchi, M., European Patent Application 171, 496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043); Liu et al. (1987) *PNAS* 84:3439–3443; Liu et al. (1987) *J Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J Natl Cancer Inst.* 80:1553–1559). A chimeric antibody can be further "humanized" by replacing portions of the animal variable region not involved in antigen binding with equivalent portions from human variable regions. General reviews of "humanized" chimeric antibodies are provided by Morrison, S. L. (1985) *Science* 229:1202–1207 and by Oi et al. (1986) *BioTechniques* 4:214. Suitable "humanized" antibodies can be produced by CDR or CEA substitution (see Winter U.S. Pat. No. 5,225,539; Jones et al. (1986) *Nature* 321:552–525; Verhoeyan et al. (1988) *Science* 239:1534; and Beidler et al. (1988) *J Immunol.* 141:4053–4060).

D. Antibody Mimetic Agents

In another embodiment, an antibody homologue of the invention is a non-antibody molecule that binds a protein of interest, thereby mimicking the binding ability of an antibody specific for the protein of interest. These agents are referred to herein as "antibody mimetic agents". An antibody mimetic agent may be a peptide that binds specifically to a protein or may be a natural ligand for a protein of interest (e.g., a ligand for a surface receptor). Additionally, the antibody mimetic agent may be only a portion of a natural ligand for the protein of interest, wherein the ligand portion retains the ability to bind to the protein of interest.

To isolate a nucleic acid molecule encoding a peptidic antibody mimetic agent that binds a protein of interest, a library of peptides (e.g., 5–20 amino acids in length) can be synthesized and screened for the ability to bind the immobilized protein. For general descriptions of peptide library construction and screening see U.S. Pat. No. 4,833,092; Scott, J. K. and Smith, G. P. (1990) *Science* 249:86–90; Devlin, J. J. et al. (1990) *Science* 249:404–407. Nucleic acid encoding the peptide can then be recovered from the library or the peptide can be sequenced by standard techniques and a nucleotide sequence encoding the peptide then deduced from the amino acid sequence of the peptide.

E. Expression of Antibody Homologues in Cells

An antibody homologue is expressed intracellularly in a host cell by introducing a recombinant expression vector containing nucleotide sequences encoding the antibody homologue into a host cell. Following isolation of antibody genes, as described above, and, if desired, further manipulation of the sequences, DNA encoding the antibody homologue can be inserted into an expression vector to facilitate transcription and translation of the antibody coding sequences in a host cell. Within the expression vector, the sequences encoding the antibody homologue are operatively linked to transcriptional and translational control sequences. These control sequences include promoters, enhancers and other expression control elements (e.g., polyadenylation signals). Such regulatory sequences are known to those skilled in the art and are described in Goeddel, *Gene Expression Technology: Methods in Enzymology* 185, Academic Press, San Diego, Calif. (1990). The expression vector and expression control sequences are chosen to be compatible with the host cell used. Expression vectors can be used to express one antibody chain (e.g., a single chain antibody) or two antibody chains (e.g., a Fab fragment). To express two antibody chains, typically the genes for both chains are inserted into the same expression vector but linked to separate control elements.

Expression of a nucleic acid in mammalian cells is accomplished using a mammalian expression vector. When used in mammalian cells, the expression vector's control functions are often provided by viral material. For example, commonly used promoters are derived from polyoma, Adenovirus 2, cytomegalovirus (CMV) and Simian Virus 40. An example of a suitable mammalian expression vector is pCDNA3 (commercially available from Invitrogen), which drives transcription via the CMV early intermediate promoter/enhancer and contains a neomycin resistance gene as a selective marker. Other examples of mammalian expression vectors include pCDM8 (Seed, B., (1987) *Nature* 329:840) and pMT2PC (Kaufman et al. (1987), *EMBO J* 6:187–195). Alternative to the use of constitutively active viral regulatory sequences, expression of an antibody homologue gene can be controlled by a tissue-specific regulatory element that directs expression of the nucleic acid preferentially in a particular cell type. Tissue-specific regulatory elements are known in the art.

In one embodiment, a recombinant expression vector of the invention is a plasmid vector. Plasmid DNA can be introduced into cells by a variety of techniques (see below), either as naked DNA or, more commonly, as DNA complexed with or combined with another substance. Alternatively, in another embodiment, the recombinant expression vector of the invention is a virus, or portion thereof, which allows for expression of a nucleic acid introduced into the viral nucleic acid. For example, replication defective retroviruses, adenoviruses and adeno-associated viruses can be used for recombinant expression of antibody homologue genes (see below). Viral mediated gene transfer into cells can be accomplished by infecting the target cell with the viral vector.

Methods for introducing nucleic acid (e.g., DNA) into cells have been described extensively in the art. Many of these methods can be applied to cells either in vitro or in vivo. Non-limiting examples of techniques which can be used to introduce an expression vector encoding an antibody homologue into a host cell include:

Adenovirus-Polylysine DNA Complexes: Naked DNA can be introduced into cells by complexing the DNA to a cation, such as polylysine, which is then coupled to the exterior of an adenovirus virion (e.g., through an antibody bridge, wherein the antibody is specific for the adenovirus molecule and the polylysine is covalently coupled to the antibody) (see Curiel, D. T., et al. (1992) *Human Gene Therapy* 3:147–154). Entry of the DNA into cells exploits the viral entry function, including natural disruption of endosomes to allow release of the DNA intracellularly. A particularly advantageous feature of this approach is the flexibility in the size and design of heterologous DNA that can be transferred to cells.

Receptor-Mediated DNA Uptake: Naked DNA can also be introduced into cells by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J Biol. Chem.* 267:963–967; and U.S. Pat. No. 5,166,320). Binding of the DNA-ligand complex to the receptor facilitates uptake of the DNA by receptor-mediated endocytosis. Receptors to which a DNA-ligand complex have targeted include the transferrin receptor and the asialoglycoprotein receptor. Additionally, a DNA-ligand complex can be linked to adenovirus capsids which naturally disrupt endosomes, thereby promoting release of the DNA material into the cytoplasm and avoiding degradation of the complex by intracellular lysosomes (see for example Curiel et al. (1991) *Proc. Natl. Acad. Sci. USA* 88:8850; and Cotten, M. et al. (1992) *Proc. Natl. Acad. Sci. USA* 89:6094–6098; Wagner, E. et al. (1992) *Proc. Natl. Acad. Sci. USA* 89:6099–6103). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Liposome-Mediated transfection ("lipofection"): Naked DNA can be introduced into cells by mixing the DNA with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) Meth. Enz. 149:157–176; Wang and Huang (1987) Proc. Natl. Acad. Sci. USA 84:7851–7855; Brigham et al. (1989) Am. J Med. Sci. 298:278; and Gould-Fogerite et al. (1989) Gene 84:429–438.

Direct Injection: Naked DNA can be introduced into cells by directly injecting the DNA into the cells. For an in vitro culture of cells, DNA can be introduced by microinjection, although this not practical for large numbers of cells. Direct injection has also been used to introduce naked DNA into cells in vivo (see e.g., Acsadi et al. (1991) Nature 332:815–818; Wolff et al. (1990) Science 247:1465–1468). A delivery apparatus (e.g., a "gene gun") for injecting DNA into cells in vivo can be used. Such an apparatus is commercially available (e.g., from BioRad).

Retroviral Mediated Gene Transfer: Defective retroviruses are well characterized for use in gene transfer for gene therapy purposes (for a review see Miller, A. D. (1990) Blood 76:271). A recombinant retrovirus can be constructed having a nucleic acid encoding a gene of interest (e.g., an antibody homologue) inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395–1398; Danos and Mulligan (1988) Proc. Natl. Acad. Sci. USA 85:6460–6464; Wilson et al. (1988) Proc. Natl. Acad. Sci. USA 85:3014–3018; Armentano et al. (1990) Proc. Natl. Acad. Sci. USA 87:6141–6145; Huber et al. (1991) Proc. Natl. Acad. Sci. USA 88:8039–8043; Ferry et al. (1991) Proc. Natl. Acad. Sci. USA 88:8377–8381; Chowdhury et al. (1991) Science 254:1802–1805; van Beusechem et al. (1992) Proc. Natl. Acad. Sci. USA 89:7640–7644; Kay et al. (1992) Human Gene Therapy 3:641–647; Dai et al. (1992) Proc. Natl. Acad. Sci. USA 89:10892–10895; Hwu et al. (1993) J Immunol. 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Adenoviral Mediated Gene Transfer: The genome of an adenovirus can be manipulated such that it encodes and expresses a gene product of interest (e.g., an antibody homologue) but is inactivated in terms of its ability to replicate in a normal lytic viral life cycle. See for example Berkner et al. (1988) BioTechniques 6:616; Rosenfeld et al. (1991) Science 252:431–434; and Rosenfeld et al. (1992) Cell 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482–6486), hepatocytes (Herz and Gerard (1993) Proc. Natl. Acad. Sci. USA 90:2812–2816) and muscle cells (Quantin et al. (1992) Proc. Natl. Acad. Sci. USA 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to many other gene delivery vectors (Berkner et al. cited supra; Haj-Ahmand and Graham (1986) J Virol. 57:267). Most replication-defective adenoviral vectors currently in use are deleted for all or parts of the viral E1 and E3 genes but retain as much as 80% of the adenoviral genetic material.

Adeno-Associated Viral Mediated Gene Transfer: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97–129). It is also one of the few viruses that may integrate its DNA into non-dividing cells, and exhibits a high frequency of stable integration (see for example Flotte et al. (1992) Am. J Respir. Cell. Mol. Biol. 7:349–356; Samulski et al. (1989) J Virol. 63:3822–3828; and McLaughlin et al. (1989) J Virol. 62:1963–1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251–3260 can be used to introduce DNA into cells. A variety of nucleic acids have been introduced into different cell types using AAV vectors (see for example Hermonat et al. (1984) Proc. Natl. Acad. Sci. USA 81:6466–6470; Tratschin et al. (1985) Mol. Cell. Biol. 4:2072–2081; Wondisford et al. (1988) Mol. Endocrinol. 2:32–39; Tratschin et al. (1984) J Virol. 51:611–619; and Flotte et al. (1993) J Biol. Chem. 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of the introduced DNA can be detected, for example, by Northern blotting, RNase protection or reverse transcriptase-polymerase chain reaction (RT-PCR). Expression of the introduced gene product (e.g., the antibody homologue) in the cell can be detected by an appropriate assay for detecting proteins, for example by immunohistochemistry.

As will be appreciated by those skilled in the art, the choice of expression vector system will depend, at least in part, on the host cell targeted for introduction of the nucleic acid. For example, nucleic acid encoding an anti-erbB2 antibody homologue (e.g., anti-erbB2 sFv) is preferably introduced into erbB2 overexpressing tumor cells. Tumor cells known to overexpress erbB2 include epithelial carcinoma cells, such as carcinoma cells derived from tissues or organs including breast, ovary, lung, gastrointestinal tract and salivary gland. Preferred expression vectors and delivery systems for introducing nucleic acid into epithelial carcinoma cells include transfection with adenoviral-polylysine DNA complexes (see Example 2) and adenoviral vector-mediated gene transfer. These delivery systems are suitable for introduction of nucleic acid into cells in vitro, or more preferably for tumor cells, in vivo.

F. Modulation of Protein Function by Intracellular Antibody Homologue Expression As described herein, the function of a protein can be modulated by expression intracellularly of an antibody homologue that binds to the protein. In a preferred embodiment of the invention, proliferation of a cell expressing a protein that stimulates expression of the cell is inhibited by introducing into the cell a nucleic acid molecule encoding an antibody homologue that binds to the protein intracellularly. Preferably, the protein that stimulates proliferation of a cell is an oncoprotein and the cell is a malignant mammalian cell. The term "oncoprotein" is intended to refer to the gene product of an oncogene. A "malignant cell" is intended to refer to a transformed, tumorigenic cell. A particularly preferred oncoprotein to be inhibited is erbB2. The term "erbB2" as used herein is intended to refer to the erbB2 oncoprotein in its various forms, including the human c-erbB2 oncoprotein (also referred to as the HER2 gene product), murine c-erbB2 (also referred to as the neu gene product) and the chicken v-erbB2 gene product.

In another preferred embodiment, cell surface expression of a protein normally expressed on the surface of a cell is inhibited by introducing into the cell a nucleic acid molecule encoding an antibody homologue that binds to the protein within an intracellular compartment (e.g., the endoplasmic reticulum). A particularly preferred cell surface protein to be inhibited is erbB2.

In yet another embodiment, the invention provides a method for inhibiting proliferation or survival of erbB2-overexpressing tumor cells in a mammal. The method involves introducing into the tumor cells a nucleic acid molecule encoding an antibody homologue, wherein the antibody homologue is expressed intracellularly and binds to erbB2 intracellularly within an intracellular compartment of the tumor cells, thereby inhibiting proliferation or survival of the tumor cells. The term "mammal" is intended to encompass animal species that are susceptible to erbB2-overexpressing tumors and may include humans, monkeys, dogs, cats, rats, mice, etc. A nucleic acid molecule encoding an antibody homologue can be introduced into tumor cells in a mammal using one of a number of techniques suitable for introduction of exogenous DNA into cells in vivo as described previously herein (see Section E, above).

The functional outcome of intracellular antibody expression on the subsequent expression and/or function of the protein targeted for antibody binding (referred to as the target protein) can be assessed by suitable assays that monitor the expression and/or function of the target protein. With regard in particular to erbB2, the effect of intracellular anti-erbB2 sFv expression can be examined using an erbB2 overexpressing epithelial carcinoma cell line, such as SKOV3, into which an anti-erbB2 sFv has been introduced in vitro, using assays as described herein. Cell surface expression of erbB2, or other membrane target protein, following intracellular antibody homologue expression can be assessed, for example, by standard immunohistochemistry techniques using an antibody specific for the target protein (see Example 3). The subcellular localization of the target protein and/or the antibody homologue can be determined, for example, by immunoelectron microscopy (e.g., the antibody homologue can be labeled with gold particles and the target protein with silver particles, or vice versa). Additionally, the effect of intracellular antibody expression on cellular proliferation can be assessed by immunohistochemistry using an antibody against a proliferation-associated antigen, such as the nuclear antigen Ki-67 (see Example 4). Alternatively, cell proliferation can be measured using commercially available cell proliferation assays (e.g., the Cell Titer 96 AQueous Non-Radioactive Cell Proliferation Assay from Promega; see Example 4). The effect of intracellular anti-erbB2 expression on cell survival can be assessed by quantitating the number of stable cell clones obtainable after transfection of cells with the anti-erbB2 expression vector (see Example 5). As demonstrated in the Examples, intracellular anti-erbB2 sFv expression markedly reduces expression of erbB2 on the surface of an erbB2 overexpressing carcinoma cell line (SKOV3) and, moreover, markedly inhibits both cell proliferation and cell survival.

The functional outcome of intracellular anti-erbB2 antibody homologue expression on tumor cell growth and survival in a mammal can be assessed in vivo using animal model systems that may be predictive of therapeutic efficacy in humans. For example, carcinoma cells (e.g., SKOV3 cells) are transfected with the anti-erbB2 expression vector ex vivo and then transferred into mice (e.g., athymic nude mice). Tumor growth, as measured by tumor size, is monitored over time (e.g., 80 days), with reduced or absent tumor growth indicating that intracellular anti-erbB2 expression inhibits cell proliferation and/or survival (see Example 6). Carcinoma cells can also be modified in vivo to express an anti-erbB2 sFv intracellularly. Carcinoma cells (e.g., SKOV3) are first injected into the peritoneum of mice and then an adenovirus-polylyine DNA complex, comprising the anti-erB2 sFv expression vector, is also injected into the peritoneum. Tumor growth can be monitored in vivo and/or carcinoma cells can be recovered from the animal and their survival assessed in vitro.

G. Compositions of the Invention

The invention provides isolated nucleic acid molecules encoding ER-expressed forms of anti-erbB2 antibody homologues. The term "isolated" as used herein refers to a nucleic acid substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived. The term "nucleic acid" is intended to encompass DNA and RNA and may be single or double-standed. A preferred nucleic acid molecule is double-stranded DNA. In a preferred embodiment, the isolated nucleic acid molecule comprises a first nucleotide sequence encoding a signal sequence operatively linked in a 5' to 3' direction by a phosphodiester bond to a second nucleotide sequence encoding a single chain Fv fragment that binds an erbB2 oncoprotein. The signal sequence directs expression of a protein (e.g., the anti-erbB2 sFv) comprising the signal sequence to an endoplasmic reticulum. Preferably, the signal sequence comprises an amino acid sequence shown in SEQ ID NO: 3. Preferably, the anti-erbB2 sFv comprises an amino acid sequence shown in SEQ ID NO: 5, and is encoded by a nucleotide sequence shown in SEQ ID NO: 4.

The invention further provides recombinant expression vectors comprising a nucleic acid molecule encoding an ER-expressed forms of an anti-erbB2 antibody homologue (e.g., an ER-expressed form of an anti-erbB2 sFv). As used herein, the term "vector" refers generally to a nucleic acid molecule capable of transporting another nucleic acid to which it has been linked. The term "recombinant expression vector" refers to a vector which is capable of directing expression (i.e., transcription) of a nucleic acid to which it has been linked. The recombinant expression vector can be, for example, a plasmid vector or a viral vector.

The invention still further provides host cells into which a recombinant expression vector of the invention has been introduced. Preferably, the host cell is a mammalian cell, more preferably a malignant mammalian cell, even more preferably, an epithelial carcinoma cell. In various embodiments, the epithelial carcinoma cell may be of a tissue or organ selected from the group consisting of breast, ovary, gastrointestinal tract, lung and salivary gland.

H. Other Embodiments of the Invention

While the invention has been described in particular with regard to inhibition of erbB2 expression and function in tumor cells (e.g., carcinoma cells), the intracellular antibody approach described herein can equally be applied to other target proteins to modulate their expression and/or function. For example, antibody homologues against other cell surface receptors, such as receptor tyrosine kinases in addition to erbB2, can be expressed intracellularly in the ER to inhibit the surface expression and function of the receptor tyrosine kinases in accordance with the present invention. As described herein, ER-expressed forms of antibody homologues are prepared by linkage of nucleic acid encoding an appropriate signal sequence to nucleic acid encoding the antibody homologue. Examples of receptor tyrosine kinases that can be inhibited according to the invention include the epidermal growth factor receptor (EGFR), the platelet derived growth factor receptor (PDGFR), the sis,fms and kit oncogene products and other kinases such as those described in Hanks, S. K. et al. (1988) *Science* 241:42–52.

In addition to modulating the expression and/or function of cell surface membrane proteins by binding to their immature forms during transit through the ER, the ER-expressed forms of antibody homologues described herein can also be used to modulate the function of soluble, secreted proteins by binding to their intracellular forms during transit through the ER. Accordingly, in another embodiment, the invention provides a method for inhibiting the function of a soluble secreted protein by expressing intracellularly in the ER an antibody homologue that binds to the secreted protein.

Furthermore, the invention is not limited to modulating the expression and/or function of ER-expressed proteins, but rather can also be applied to modulating the function of proteins found in other cellular locations. For example, an antibody homologue can be targeted intracellularly to the cytosol or the nucleus to modulate the function of cytosolic or nuclear proteins, respectively. To target an antibody homologue to the cytoplasm of a host cell, to thereby modulate the function of a cytosolic protein, a nucleic acid molecule encoding an antibody homologue which lacks a signal sequence is introduced into the host cell.

Alternatively, to express an antibody homologue in the nucleus of a host cell, to thereby modulate the function of a nuclear protein, a nucleic acid molecule encoding a nuclear-targeted form of an antibody homologue is introduced into the host cell. A nucleotide sequence encoding a nuclear localization sequence (NLS) from a nuclear protein (e.g., from an SV40 T antigen) can be operatively linked to a nucleotide sequence encoding an antibody homologue to thereby target the antibody homologue to the nucleus when expressed in a mammalian host cell.

This invention is further illustrated by the following examples which should not be construed as limiting. The contents of all references, patents and published patent applications cited throughout this application are hereby incorporated by reference.

EXAMPLE 1

Construction of an Anti-erbB2 Single Chain Antibody (sFv) Expression Vector

As a means to prevent maturational processing of the nascent erbB2 protein during synthesis, a gene construct was designed which encodes an anti-erbB2 single chain immunoglobulin (sFv) linked to a signal sequence. It was hypothesized that expression of this construct in target cells would result in an ER localized form of the sFv which would entrap erbB2 during synthesis thus preventing its subsequent translocation to the cell surface. The anti-erbB2 sFv construct is referred to herein as pGT21. As a control, a similar anti-erbB2 sFv construct was designed which lacked a signal sequence which would dictate its localization to the ER (referred to as pGT20). The pGT20 and pGT21 constructs are diagrammed schematically in FIG. 1. A third construct encoding an ER-form of a human anti-idiotype sFv (4B5) was also prepared as a control (this construct is referred to as pGT23).

Expression plasmids were derived containing gene constructs encoding single chain immunoglobulins directed against human erbB2. For this purpose, the eukaryotic expression vector pCDNA3 (obtained commercially from Invitrogen) was used. This vector drives transcription via the CMV early intermediate promoter/enhancer and contains a neomycin resistance gene as a selective marker. The anti-erbB2 sFv plasmid e23scFv (described in Batra, J. K. et al. (1992) *Proc. Natl. Acad. Sci. USA* 89:5867–5871) was obtained from Oncologix and used for the derivation of subsequent constructs. Genetic modifications of the anti-erbB2 sFvs were carried out employing standard polymerase-chain reaction (PCR) methods. PCR was performed using Pfu polymerase (Stratagene) with the 5' primer: AGGGTACCATGGACGTCCAGCTGACC (SEQ ID NO: 1), and the 3' primer: GCTCTAGATTAGGAGACG-GTGACCGTGGTCC (SEQ ID NO: 2). The PCR product, containing an ATG initiation codon followed by the sFv gene, was subject to digestion with the restriction endonucleases KpnI and XbaI, and cloned into pCDNA3. This construct, pGT20, would be predicted to express a non-endoplasmic reticulum (ER) form of the sFv, as the coding region lacks a signal sequence to achieve localization of the sFv to the ER. To ensure that the sFv was directed to the ER, the coding sequence for a leader peptide (amino acid sequence: MKSHSQVFVFLLLCVSGAHG) (SEQ ID NO: 3) was incorporated into the 5' end of the anti-erbB2 sFv coding sequence by PCR methods. This PCR product was also cloned into the KpnI/XbaI sites of pCDNA3. This construct is named pGT21. The constructs were confirmed by standard dideoxy sequencing.

EXAMPLE 2

Transfection of Carcinoma Cells with Anti-erbB2 sFv Expression Vectors

To determine the effect of intracellular expression of anti-erbB2 sFv on cell surface erbB2 expression, cell proliferation and cell survival, the anti-erbB2 sFv expression vectors and control vector described in Example 1 were introduced into carcinoma cells. The human ovarian carcinoma cell lines, SKOV3 and SW626, and the human epithelial carcinoma cell line HeLa were obtained from the American Type Culture Collection (Rockville, Md.). Cells were maintained in complete medium consisting of Dulbecco's modified Eagles medium (DMEM) supplemented with L-glutamine (300 µg/ml), penicillin (100 I.U./ml), streptomycin (25 µg/ml) and 10% fetal calf serum (PAA) at 37° C. in a humidified 5% $CO_2$ atmosphere. The SKOV3 ovarian carcinoma cell line is known to overexpress the erbB2 protein on its surface. The SW626 ovarian carcinoma cell line is also known to overexpress cell surface erbB2, however not at the same magnitude as for the SKOV3 cell line. The HeLa epithelial carcinoma cell line does not overexpress cell surface erbB2.

For transient transfection of cells, the method of adenovirus-polylysine was employed (Curiel, D. T., et al. (1992) *Human Gene Therapy* 3:147–154). Adenovirus-polylysine (AdpL) was prepared by linkage of the replication defective adenovirus dl1014 to poly-L-lysine (Sigma) by the EDC method (Cristiano, R. J., et al. (1993) *Proc. Natl. Acad. Sci. USA* 90:11548–11552). Viral-polylysine conjugates were diluted to a concentration of $1\times10^{11}$ viral particles per ml as described in Curiel, D. T., et al. (cited supra). Conjugate-DNA complexes were then formed by the sequential addition of 100 µl of AdpL, 6.0 µg of plasmid DNA diluted in 200 µl 150 mM NaCl, 20 mM HEPES, pH 7.3 (HBS) and 4.0 µg poly-L-lysine (from Sigma Chemical Co., St. Louis, Mo.) diluted in 200 µl HBS. A volume of conjugate-DNA complex containing 2.0 µg of plasmid DNA was then delivered to target cells in 6 well tissue culture dishes in 1.0 ml of medium containing 2% FCS. Incubation was carried out for 1 hour at 37° C., after which 2 ml of complete medium was added to cells and incubation continued for 48, 72, or 96 hours. Preliminary experiments demonstrated that the adenovirus-polylysine-DNA complexes containing a β-galactosidase reporter gene (pCMVβ) accomplished detectable levels of reporter gene expression in >90% of targeted cells.

Plasmid DNAs were stably transfected into target cells by the lipofectAMINE method (GIBCO/BRL, Grand Island, N.Y.) using conditions described by the manufacturer. Briefly, lipid/DNA complexes consisting of 40 µg lipofectAMINE and 4.0 µg plasmid DNA were delivered to cells at ~50% confluency in 6.0 cm tissue culture dishes in a volume of 1.0 ml of OptiMEM medium (GIBCO/BRL). After an 18 hr incubation, the transfection medium was removed and replaced with complete medium and incubation continued for an additional 48 hrs. Cells were then split into selective medium containing Geniticin (GIBCO BRL) at 1 mg/ml. The cells were maintained for 21 days at which time the number of resistant colonies was determined by standard crystal violet staining.

EXAMPLE 3

Downregulation of Cell Surface erbB2 Expression on Ovarian Carcinoma Cells by Intracellular Expression of Anti-erbB2 sFv The plasmid DNAs pCDNA3, pGT20, and pGT21 were transfected into the erbB2 over-expressing ovarian carcinoma cell line SKOV3 using the adenovirus-polylysine (AdpL) method as described in Example 2. At various times after transfection, the cells were evaluated for cell surface expression of erbB2 using the technique of immunocytochemistry employing an anti-human erbB2 monoclonal antibody as follows: $5\times10^4$ cells were cytocentrifuged onto superfrost slides (commercially obtained from Fisher) and fixed for 10 minutes in 4% paraformaldehyde in TBS (Tris-buffered saline). After appropriate blocking steps, a rabbit anti-human c-erbB2 antibody (DAKO) was employed at the manufacturers' pre-diluted concentration and an ABC peroxidase system (commercially obtained from Vector Labs) was utilized for immunocytochemical detection of cell surface c-erbB2-protein.

Figure 2A:
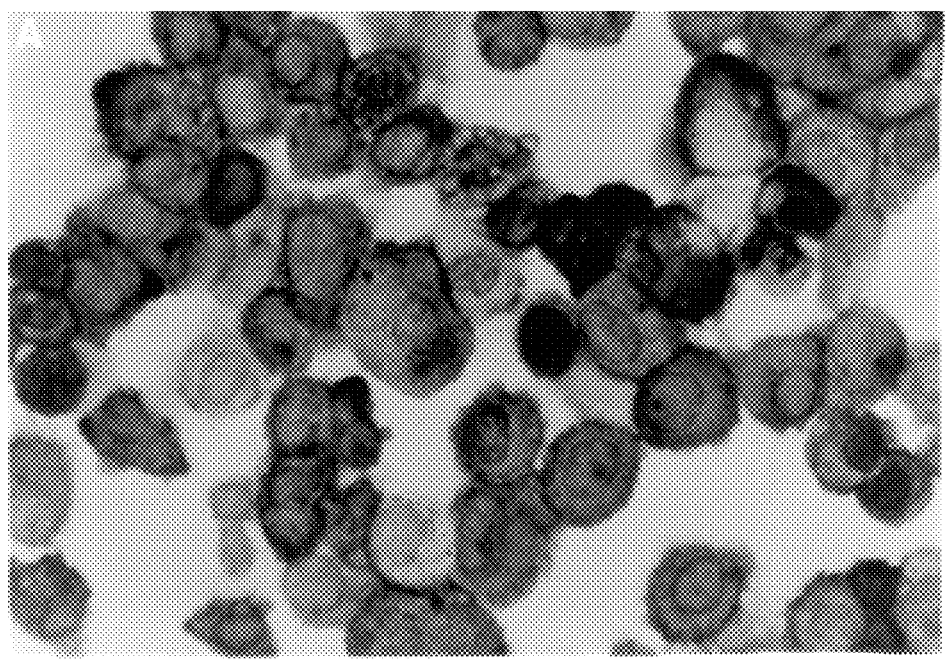
FIGS. 2A–C are photographs of immunocytochemistry slides of human ovarian carcinoma SKOV3 cells reacted with a rabbit anti-human anti-erbB2 monoclonal antibody, depicting the effect of intracellular anti-erbB2 sFv expression on cell surface expression of erbB2 protein. Panel A shows SKOV3 cells transfected with control plasmid pCDNA3. Panel B shows SKOV3 cells transfected with pGT20 (non-ER form of anti-erbB2 sFv). Panel C shows SKOV3 cells transfected with pGT21 (ER form of anti-erbB2 sFv). Magnification is 400X.
Figure 2B:
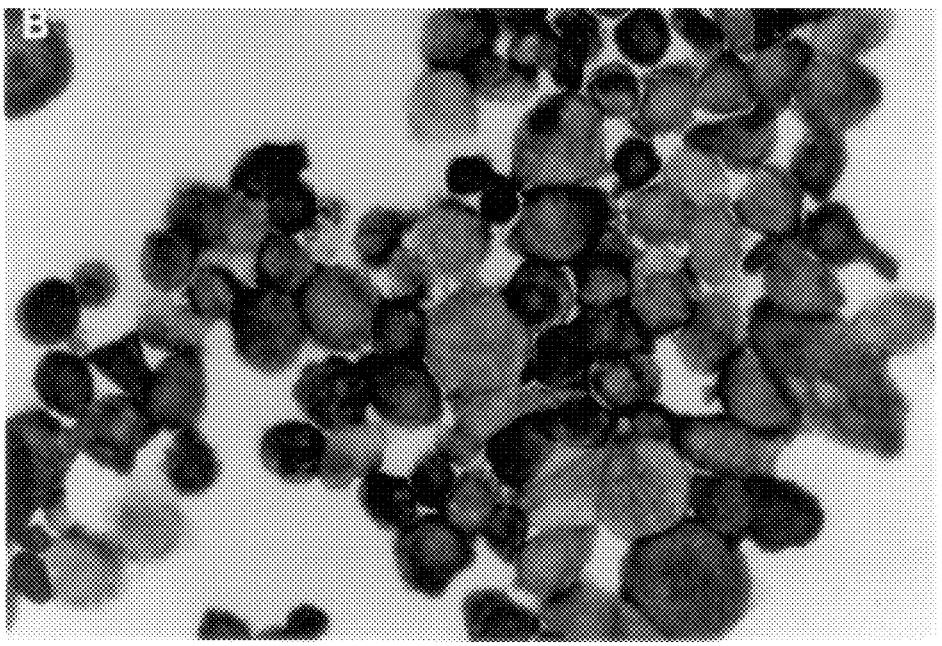
Figure 2C:
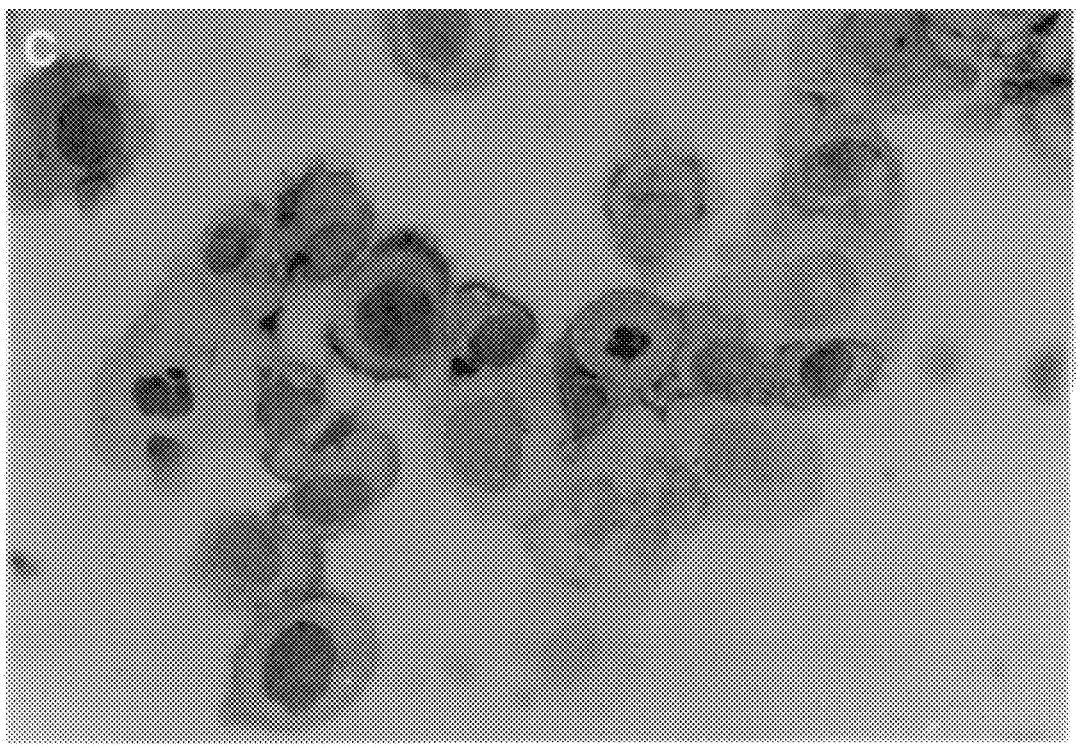

The results of the immunocytochemistry assays are shown in FIG. 2, panels A–C. SKOV3 cells transfected with the irrelevant plasmid DNA pCDNA3 exhibited high levels of cell surface erbB2, as would be expected (FIG. 2, panel A). Additionally, SKOV3 cells transfected with the non-ER form of the anti-erbB2 sFv (pGT20) exhibited levels of cell surface erbB2 similar to the control (FIG. 2, panel B). In contrast, SKOV3 cells transfected with pGT21, which encodes an ER form of the anti-erbB2 sFv, demonstrated marked down-regulation of cell surface erbB2 expression (FIG. 2, panel C). This down-regulation appeared to be time-dependent, with cell surface erbB2 levels progressively declining from 48 to 96 hours post-transfection. At 96 hours post-transfection, fewer than 10% of the pGT21 transfected cells exhibited detectable levels of cell surface erbB2 protein. The cells otherwise appeared morphologically indistinguishable from the control groups.

To exclude the possibility that anti-erbB2 sFv secreted by transfected cells could exert a "paracrine effect" on non-transfected cells, additional experiments were performed. SKOV3 cells were transfected as described above with pCDNA3, pGT20 and pGT21. After 72 hours, supernatant was collected and delivered to non-transfected SKOV3 cells which were then analyzed for cell surface erbB2 expression by immunocytochemistry, as described above. In this analysis, none of the transfected cell supernatants exhibited the capacity to down-regulate cell surface erbB2 expression. Thus, intracellular expression of an anti-erbB2 sFv is capable of effective down-modulation of cell-surface erbB2. The fact that only the ER form of the erbB2 sFv was capable of achieving this effect is consistent with the hypothesis that the nascent erbB2 was entrapped in the endoplasmic reticulum during synthesis.

EXAMPLE 4

Inhibition of Proliferation of Ovarian Carcinoma Cells by Intracellular Expression of Anti-erbB2 sFv To determine whether cell surface expression of erbB2 correlates with cellular proliferation rates, the effect of the various sFv gene constructs on tumor cell proliferation was evaluated. For this analysis, immunocytochemistry for the proliferation-associated nuclear antigen Ki67 was employed. A mouse monoclonal antibody which recognizes an epitope on the proliferating cell antigen Ki67, in combination with an alkaline phosphate system (APAAP-DAKO) was used for immunocytochemical detection of cell proliferation. The experiments described in this Example were performed in parallel with those for detection of cell surface erbB2 described in Example 3. For further description of the use of the Ki67 antigen to analyze cell proliferation see Gerdes, J., et al. (1984) *J Immunol.* 133:1710–1715.

Figure 3A:
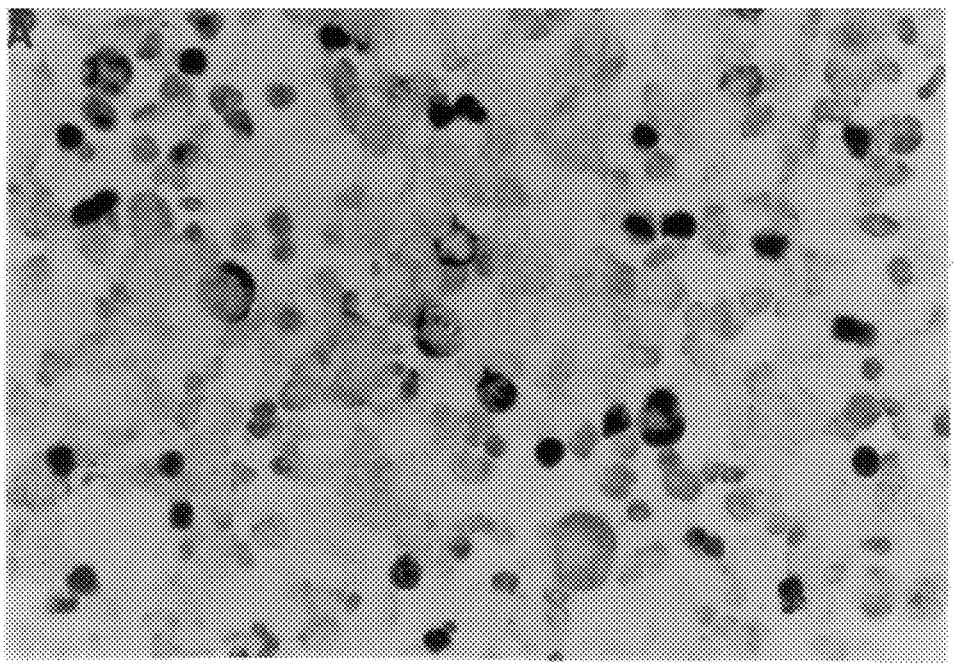
FIGS. 3A–C are photographs of immunocytochemistry slides of human ovarian carcinoma SKOV3 cells reacted with a mouse anti-Ki-67 monoclonal antibody, depicting the effect of intracellular anti-erbB2 sFv expression on nuclear expression of the proliferation-associated marker Ki-67. Panel A shows SKOV3 cells transfected with control plasmid pCDNA3. Panel B shows SKOV3 cells transfected with pGT20 (non-ER form of anti-erbB2 sFv). Panel C shows SKOV3 cells transfected with pGT21 (ER form of anti-erbB2 sFv). Magnification is 400X.
Figure 3B:
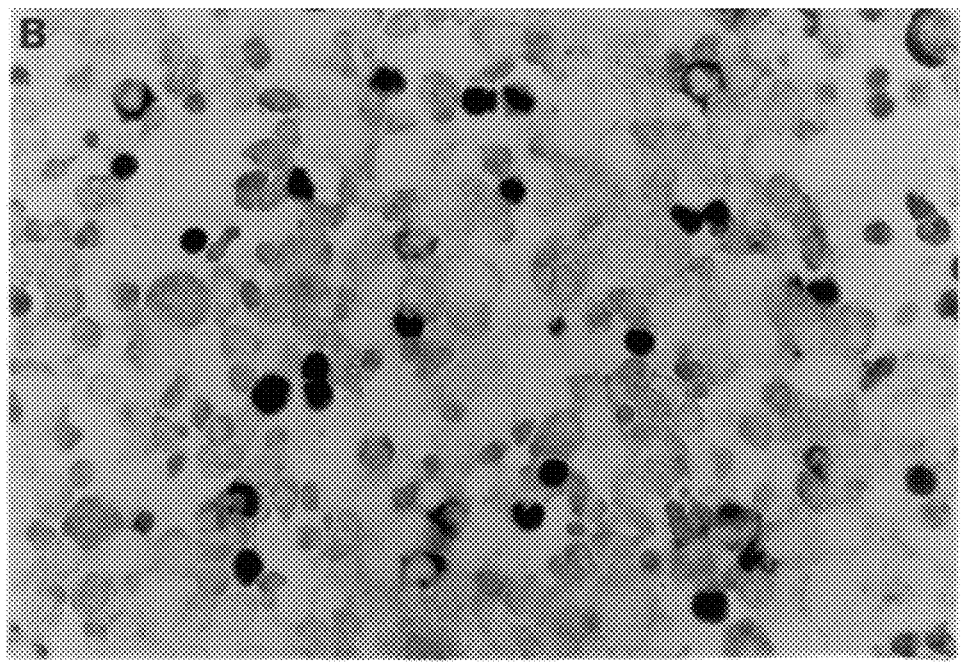
Figure 3C:
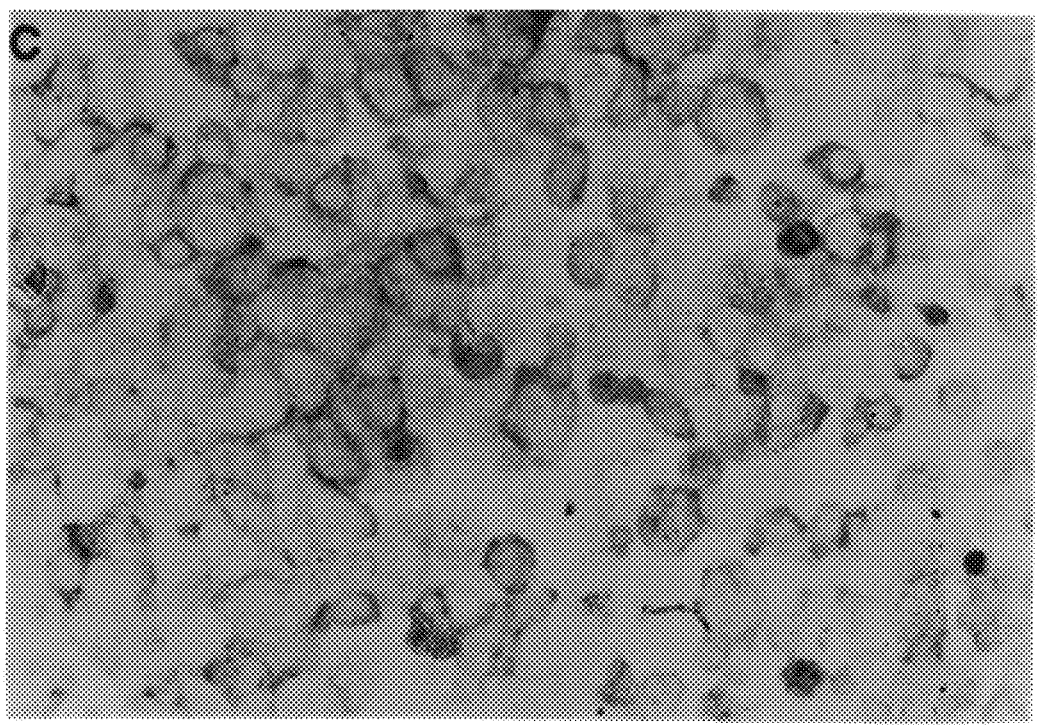

The results of the cell proliferation immunocytochemistry assays are shown in FIG. 3, panels A–C. Transfection of SKOV3 cells with the control plasmid pCDNA3 resulted in the immunocytochemical detection of active cellular proliferation (FIG. 3, panel A). In addition, transfection with the non-ER form of the anti-erbB2 sFv (pGT20) did not result in any net change in cell proliferation (FIG. 3, panel B). In marked contrast, transfection of the erbB2 over-expressing cell line SKOV3 with the ER form of the anti-erbB2 sFv (pGT21) resulted in a dramatic inhibition of cellular proliferation as determined by Ki-67 immunohistochemistry (FIG. 3, panel C). The percentage of cells exhibiting nuclear staining in this group was significantly reduced, paralleling the percentage decrease of cell surface erbB2 protein.

The degree of inhibition of cell proliferation was also assessed employing a quantitative assay. Quantitative assessment of cell proliferation was carried out using the Cell Titer 96 AQueous Non-Radioactive Cell Proliferation Assay (commercially obtained from Promega) using conditions recommended by the manufacturer. For this analysis, target cells were plated (5000 cells/well) and transfected with the various plasmid constructs using the AdpL method as described above. After a 96 hour incubation, the transfected cells were analyzed for released formazan by measuring absorbance at 490 nm using an ELISA plate reader. A standard curve was derived in parallel for each analysis by linear dilutions of non-transfected cells. Control studies established a linear relationship between the number of proliferative cells and the concentration of formazan released.

Figure 4:
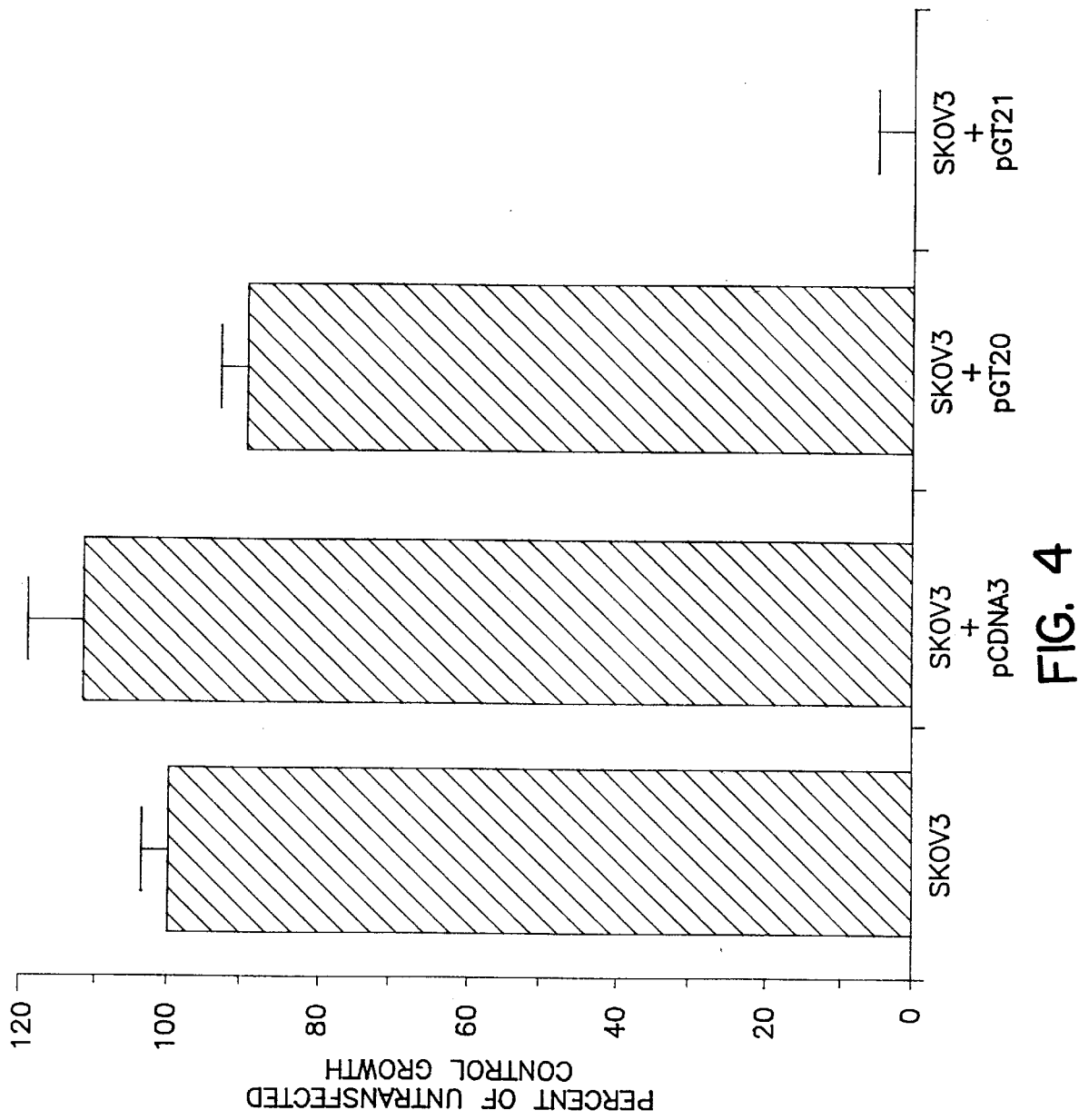
FIG. 4 is a graphic representation of the effect of intracellular expression of an ER form of anti-erbB2 sFv (pGT21) on cellular proliferation of SKOV3 cells, as compared to the effect of intracellular expression of a non-ER form of anti-erbB2 (pGT20) or a control plasmid (pCDNA3). The index of cellular proliferation was determined and compared to untransfected control cells. Experiments were performed ×12 each and results reported as mean ±S.E.

The cell proliferation results for transfected cells using the quantitative assay described above are shown graphically in FIG. 4. Transfection of SKOV3 with the control plasmid pCDNA3 did not affect the measured index of cellular proliferation compared to non-transfected control cells ($p=0.103$). Additionally, the measured index of cellular proliferation in cells transfected with the non-ER form of the anti-erbB2 sFv did not significantly differ from these two controls ($p=0.118$). Transfection of SKOV3 with the ER form of the anti-erbB2 sFv, however, resulted in a very significant inhibition of cellular proliferation ($p<0.001$). Extrapolation of the measured absorbance against the standard curve indicated that cellular proliferation was inhibited more than 95% compared to the control groups. Thus, the expression of the ER form of the anti-erbB2 sFv inhibits proliferation of erbB2 over-expressing tumor cells. It is of interest in this regard that the level of down-regulation of cell surface erbB2 mediated by the ER form of the anti-erbB2 sFv paralleled the magnitude of the observed anti-proliferative effects.

EXAMPLE 5

Reduction in Survival of Ovarian Carcinoma Cells by Intracellular Expression of Anti-erbB2 sFv As the ER-expressed anti-erbB2 sFv exhibited such a prominent anti-proliferative effect (see Example 4), it was hypothesized that it might also exhibit a direct tumoricidal effect in cells stably modified to express this gene construct. Since the plasmids pCDNA3, pGT20 and pGT21 contained neomycin selectable markers, they were used to derive stable clones as described in Example 2.

As a preliminary control, the various plasmid constructs were used to derive G418 resistant clones in HeLa, a cancer cell line not characterized by over-expression of erbB2.

After selection, the number of HeLa clones derived from transfection with pGT20 and pGT21 was not significantly different (see Table 1 below). Further, this number of clones was not significantly different when HeLa cells were transfected with the control plasmid pCDNA3.

A similar analysis was then carried out with the erbB2 over-expressing tumor line SKOV3 as the target. In this study, the number of clones derived with pGT20, the non-ER anti-erbB2 sFv, did not differ from the number derived with the control plasmid pCDNA3 (see Table 1 below). Transfection with pGT21, however, resulted in a dramatic reduction in the number of stable clones derived ($p<0.001$). It thus appeared that the expression of the ER form of the anti-erbB2 sFv was incompatible with long-term viability of transfected SKOV3 cells. Further, this effect appeared specific for erbB2 over-expressing cells as this differential clone survival was not noted for HeLa cells.

A similar analysis was carried out on another tumor target, the ovarian carcinoma cell-line SW626 (see Table 1 below). This cell line is also known to over-express cell surface erbB2, however, not at the same magnitude as for the SKOV3. In this study, the ER anti-erbB2 sFv also showed a significant reduction in the number of stable clones derived compared to the non-ER form of the anti-erbB2 sFv ($p=0.020$). The magnitude of this effect, however, was substantially less than that observed for SKOV3. It thus appears that the level of anti-neoplastic effect achieved by the anti-erbB2 sFv is correlated with the level of cell surface erbB2 over-expression on target cells.

TABLE 1

Derivation of Stable Colonies after Transfection of Epithelial Carcinoma Cell Lines with anti-erbB2 sFv Expression Plasmids

| | G418 Resistant Colonies | |
| --- | --- | --- |
| Cell Line | anti-erbB2 sFv non-ER form (pGT20) | anti-erbB2 sFv ER-form (pGT21) |
| SKOV3 | 36 | 5 |
| | 28 | 5 |
| | 23 | 3 |
| | 26 | 3 |
| | 27 | 3 |
| SW626 | 21 | 18 |
| | 24 | 16 |
| | 21 | 16 |
| | 28 | 21 |
| | 20 | 19 |
| HeLa | 68 | 77 |
| | 84 | 83 |
| | 91 | 93 |
| | 77 | 69 |
| | 88 | 89 |

To exclude the possibility that the basis for this effect could be non-specific ER localization of heterologous protein in transfected cells, similar experiments were carried out using the ER form of an sFv encoding an erbB2 irrelevant epitope (4B5). The results are shown below in Table 2.

TABLE 2

Derivation of Stable Colonies after Transfection of Epithelial Carcinoma Cell Lines with ER Forms of anti-erbB2 and anti-4B5 sFv Expression Plasmids

| Cell Line | ER form of anti-erbB2 sFv (pGT21) | ER form of anti-4B5 sFv (pGT23) |
| --- | --- | --- |
| SKOV3 | 3 | 11 |
| | 5 | 18 |
| | 3 | 16 |
| | 0 | 10 |
| | 2 | 16 |

For SKOV3, the number of stable clones derived employing the anti-4B5 sFv construct did not significantly differ from the number observed with employment of the control plasmid pCDNA3 ($p=0.09$). Thus, the observed anti-neoplastic effect of the ER form of the anti-erbB2 sFv was on the basis of its encoded antigen specificity, and not a non-specific effect related to perturbation of a sub-cellular compartment.

EXAMPLE 6

Figure 5:
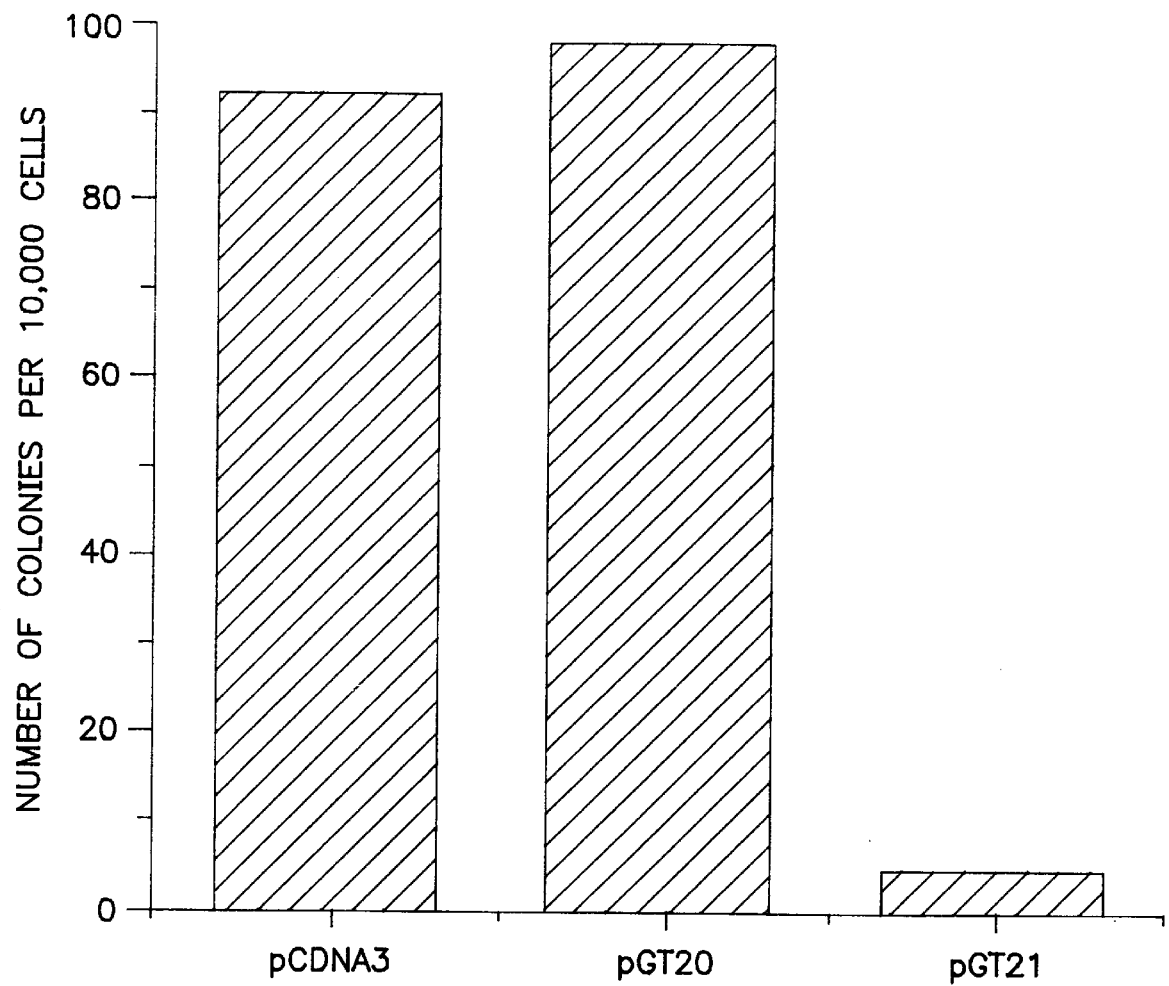
FIG. 5 is a graphic representation of the effect of intracellular expression of an ER form of anti-erbB2 sFv (pGT21) on growth of SKOV3 cells in soft agar, as compared to the effect of intracellular expression of a non-ER form of anti-erbB2 (pGT20) or a control plasmid (pCDNA3).

Reduced Tumorigenicity of Ovarian Carcinoma Cells Transfected to Express Anti-erbB2 sFv Intracellularly In this example, the ability of intracellular expression of an anti-erbB2 sFv in SKOV3 cells to inhibit the tumorigenicity of the cells was examined. In a first series of experiments, the growth of SKOV3 cells transfected with either pCDNA3 (control plasmid), pGT20 (non-ER form of anti-erbB2 sFv) or pGT21 (ER form of anti-erbB2 sFv) in soft agar was assayed by standard techniques. In this assay, the ability of cells to form colonies in soft agar (i.e., anchorage independent growth) is used as an indicator of their tumorigenicity. The results of the experiment are shown in FIG. 5. Only the ER form of anti-erbB2 sFv (pGT21) was able to inhibit growth of transfected SKOV3 cells in soft agar, as compared to the pCDNA3 control plasmid. Transfection of SKOV3 cells with pGT21 inhibited colony formation by greater than 95%.

Figure 6:
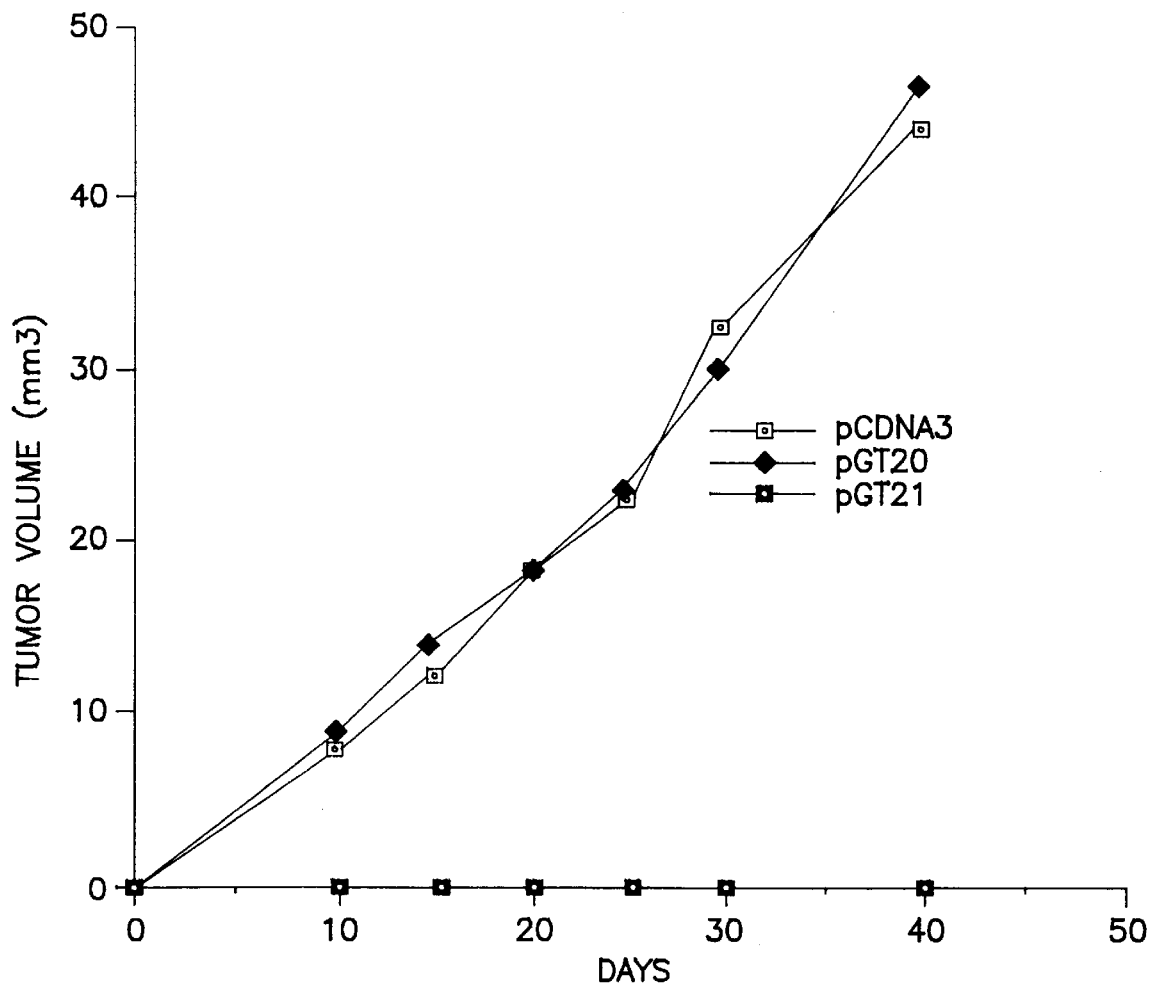
FIG. 6 is a graphic representation of the effect of intracellular expression of an ER form of anti-erbB2 sFv (pGT21) on tumorigenicity of SKOV3 cells transplanted subcutaneously into nude mice, as compared to the effect of intracellular expression of a non-ER form of anti-erbB2 (pGT20) or a control plasmid (pCDNA3).

As an additional, independent index of anchorage independent growth, tumor formation was evaluated in athymic nude mice. SKOV3 cells transfected with either pCDNA3, pGT20 or pGT21 were transplanted subcutaneously into nude mice. Tumor growth as assessed by measuring tumor size (i.e., tumor volume in $mm^3$) over a period of 40 days. The results of this experiment are shown in FIG. 6. SKOV3 cells transfected with either pCDNA3 or pGT20 formed rapidly growing subcutaneous tumors in nude mice. In contrast, the pGT21 transfected SKOV3 cells did not form detectable tumors in nude mice for the duration of the experiment (i.e., greater than 40 days post transplantation). These findings, in addition to the results of the soft agar growth assay, indicate that the ER form of the anti-erbB2 sFv is capable of abrogating the tumorigenicity of erbB2-overexpressing malignant cells.

Figure 7:
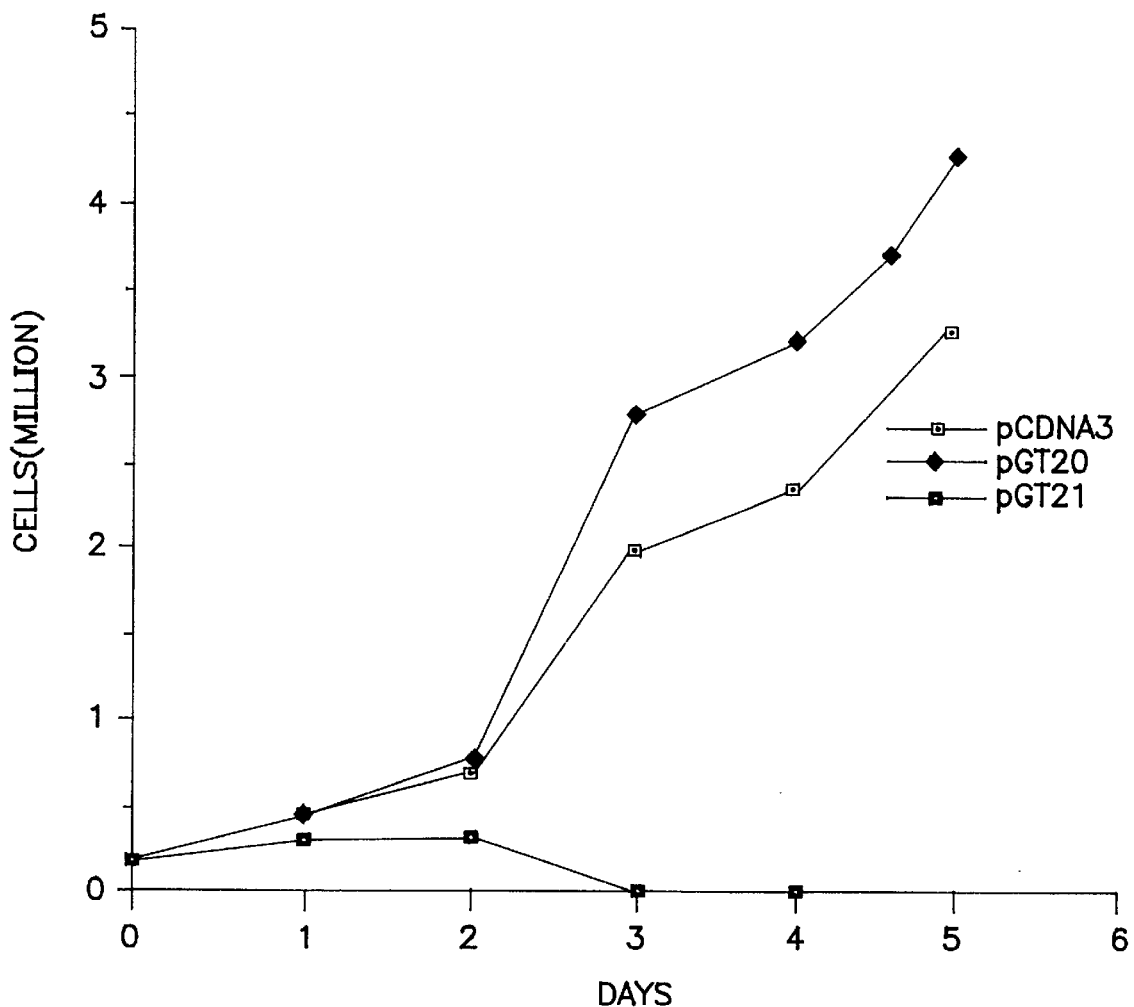
FIG. 7 is a graphic representation of the growth curves of SKOV3 cells transfected with an expression vector encoding an ER form of anti-erbB2 sFv (pGT21), a non-ER form of anti-erbB2 sFv (pGT20) or a control plasmid (pCDNA3).
Figure 8:
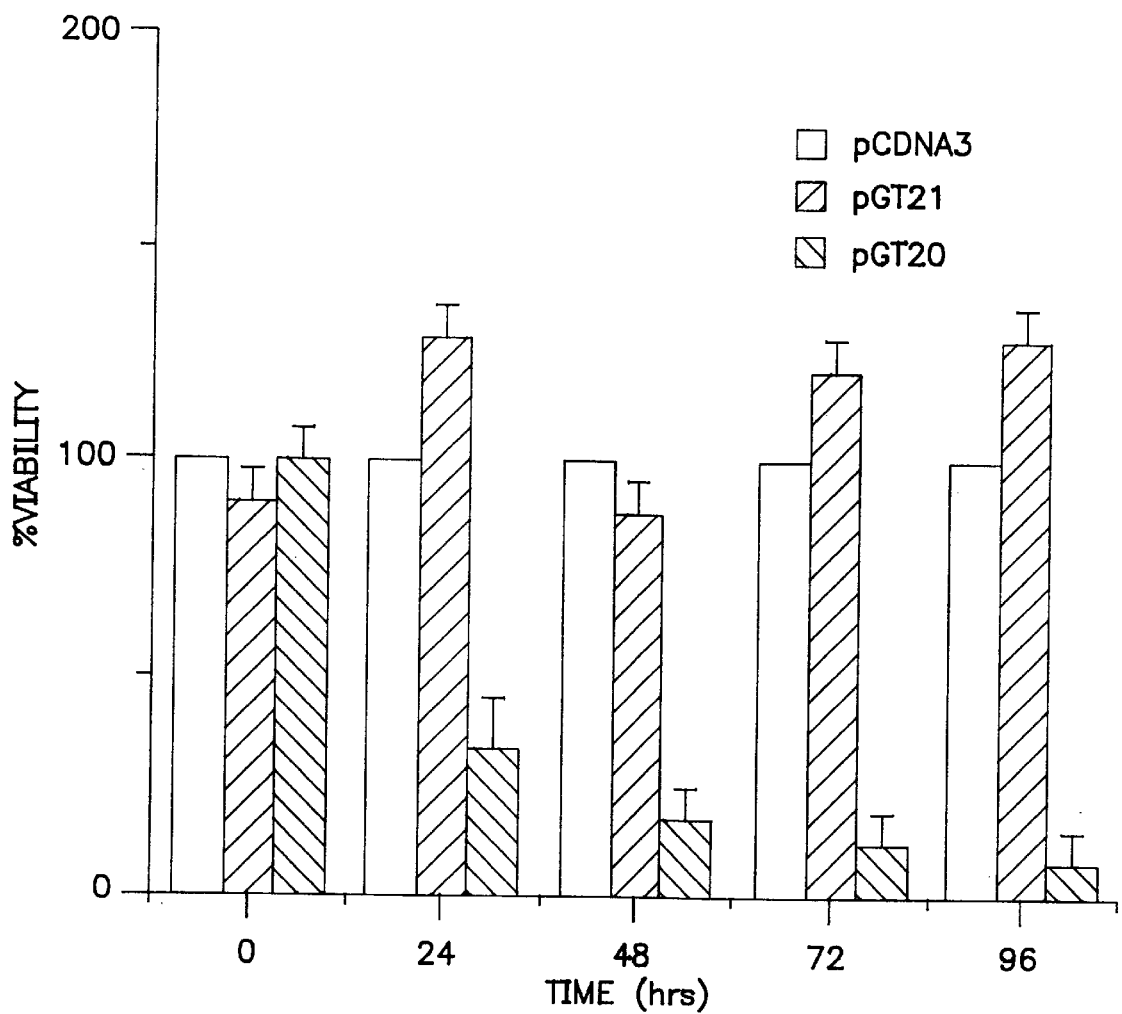
FIG. 8 is a graphic representation of the effect of intracellular expression of an ER form of anti-erbB2 sFv (pGT21) on cell viability of SKOV3 cells 24, 48, 72 or 96 hours after transfection, as compared to the effect of intracellular expression of a non-ER form of anti-erbB2 (pGT20) or a control plasmid (pCDNA3).

To determine the basis of this effect, cell growth parameters in response to intracellular expression of the ER form of anti-erbB2 sFv (pGT21), compared to control plasmids (pCDNA3 and pGT20) were evaluated. First, cell growth curves were determined over a 6 day period. The results are illustrated graphically in FIG. 7, in which cell number in millions is plotted against time in days. Transfection of the SKOV3 cells with either pCDNA3 or pGT20 did not affect the normal temporal increase in cell number. In contrast, tumor cell number decreased with time in the pGT21 transfected group. This analysis suggested that pGT21 transfection not only inhibited proliferation of the SKOV3 cells but also eradicated viable cells. To establish this, SKOV3 cells were transfected with either pCDNA3, pGT20 or pGT21 and at various time points after transfection (e.g., 24, 48, 72 and 96 hours) cell viability was directly evaluated employing an XTT assay for cell viability. The results are shown in FIG. 8. Neither pCDNA3 nor pGT20 exhibited an effect on cell viability. In contrast, cell viability was dramatically diminished upon transfer of the pGT21 construct. For example, at 96 hours post-transfection, greater than 95% of the SKOV3 cells were non-viable (i.e., had been killed). This indicates that the inhibition of erbB2 by the intracellular anti-erbB2 sFv is lethal to the SKOV3 cells. Thus, the specificity of the effect observed for anti-erbB2 sFv inhibition of erbB2 can be exploited for selective killing of target cancer cells.

Figure 9:
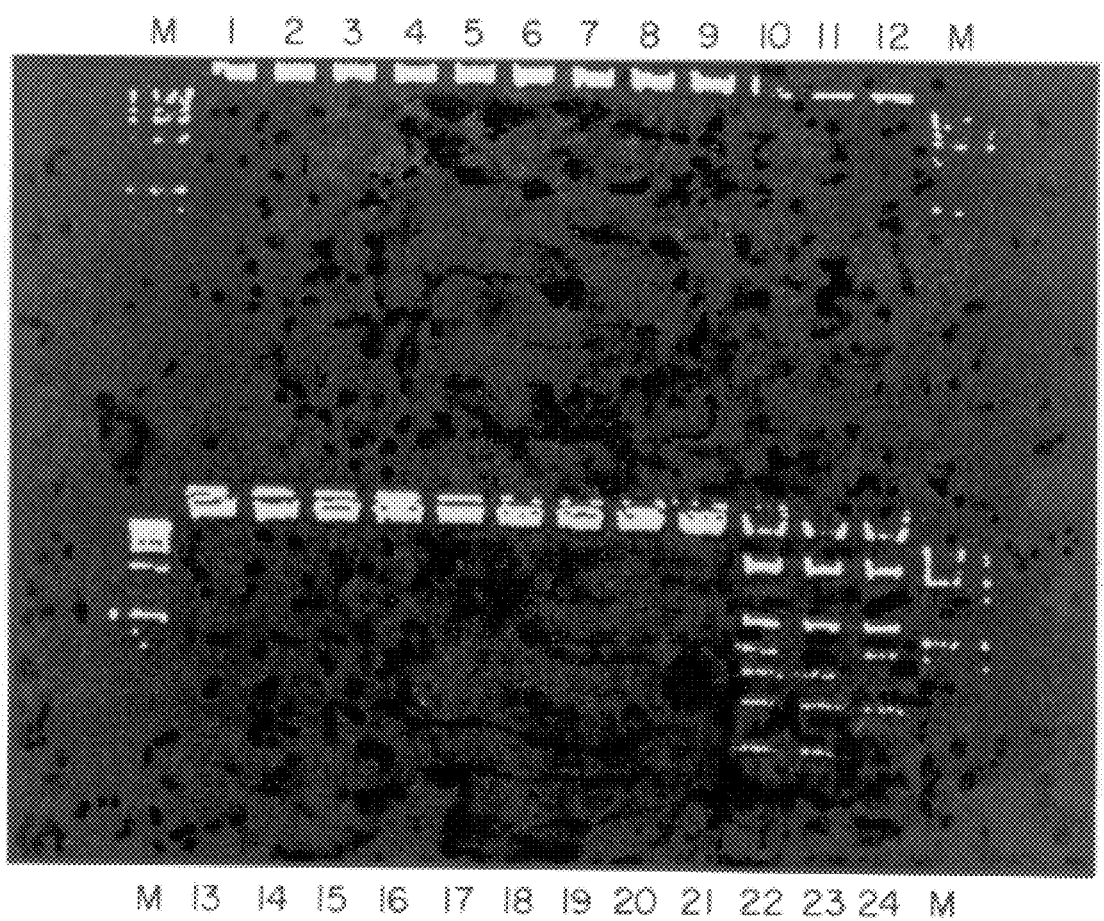
FIG. 9 is a photograph of an agarose gel depicting DNA fragmentation in SKOV3 cells following intracellular expression of an ER form of anti-erbB2 sFv.

To examine the basis of the effect of the intracellular ER form of anti-erbB2 sFv on cell viability, assays measuring apoptosis (or programmed cell death) were performed. DNA fragmentation was used as an indicator of apoptosis. SKOV3 or HeLa cells were transfected with pCDNA3, pGT20 or pGT21 and at various time points after transfection (e.g., 24, 48, 72 and 96 hours), DNA fragmentation was assessed by agarose gel electrophoresis of ethidium bromide stained DNA. The results are shown in FIG. 9, which depicts a photograph of an agarose gel. Lanes 1–4 are HeLa cells 24 hours (lane 1), 48 hours (lane 2), 72 hours (lane 3) or 96 hours (lane 4) after transfection with pCDNA3; lanes 5–8 are HeLa cells 24 hours (lane 5), 48 hours (lane 6), 72 hours (lane 7) or 96 hours (lane 8) after transfection with pGT20; lanes 9–12 are HeLa cells 24 hours (lane 9), 48 hours (lane 10), 72 hours (lane 11) or 96 hours (lane 12) after transfection with pGT21; lanes 13–16 are SKOV3 cells 24 hours (lane 13), 48 hours (lane 14), 72 hours (lane 15) or 96 hours (lane 16) after transfection with pCDNA3; lanes 17–20 are SKOV3 cells 24 hours (lane 17), 48 hours (lane 18), 72 hours (lane 19) or 96 hours (lane 20) after transfection with pGT20; lanes 21–24 are SKOV3 cells 24 hours (lane 21), 48 hours (lane 22), 72 hours (lane 23) or 96 hours (lane 24) after transfection with pGT21; lanes marked M are size markers. No DNA fragmentation was observed in HeLa cells transfected with any of the constructs (lanes 1–12) or in SKOV3 cells transfected with either pCDNA3 or pGT20 (lanes 13–20). However, prominent DNA fragmentation was induced in SKOV3 cells transfected with pGT21 (lanes 21–24). Thus, the effect of erbB2 inhibition by intracellular expression of an ER form of anti-erbB2 sFv is to trigger apoptosis in erbB2 overexpressing tumor cells.

In summary, the data presented in Examples 3, 4, 5 and 6 demonstrate that expression intracellularly of an ER-expressed form of anti-erbB2 sFv in an erbB2 overexpressing carcinoma cells (e.g., the ovarian carcinoma cell line SKOV3) results in decreased cell surface expression of erbB2, decreased cellular proliferation, decreased cell survival and decreased tumorigenicity.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for killing a cell expressing a protein that stimulates proliferation of said cell, comprising the steps of introducing into said cell a nucleic acid molecule encoding an antibody homologue, wherein said antibody homologue is expressed intracellularly and binds to said protein intracellularly, to thereby kill said cell, wherein said cell is a malignant mammalian cell, wherein said protein is an oncoprotein, wherein said oncoprotein is normally expressed in mature form on the cell surface, wherein said oncoprotein is erbB-2.

2. The method of claim 1, wherein the cell is a malignant mammalian cell and the protein is an oncoprotein.

3. The method of claim 2, wherein the oncoprotein is normally expressed in mature form on the cell surface and the antibody homologue binds to the oncoprotein within an intracellular compartment of the cell.

4. The method of claim 1, wherein the antibody homologue is a single chain Fv fragment.

5. The method of claim 1, wherein the antibody homologue is a Fab Fragment.

6. The method of claim 1, wherein nucleic acid molecule is a recombinant expression vector.

7. The method of claim 6, wherein the recombinant expression vector is a viral vector.

8. The method of claim 6, wherein the recombinant expression vector is a plasmid vector.

9. The method of claim 1, wherein the antibody homologue binds to the oncoprotein intracellularly in the endoplasmic reticulum.

10. The method of claim 1, wherein the malignant cell is an epithelial carcinoma cell.

11. The method of claim 10, wherein the epithelial carcinoma cell is of a tissue or organ selected from the group consisting of breast, ovary, gastrointestinal tract, lung and salivary gland.

12. The method of claim 1, wherein the nucleic acid molecule is introduced into the malignant cell in vivo in a mammal.

13. A method for inhibiting survival of erbB2-overexpressing tumor cells in a mammal, comprising introducing into the tumor cells a nucleic acid molecule encoding an antibody homologue, wherein the antibody homologue is expressed intracellularly and binds to erbB2 intracellularly within an intracellular compartment of the tumor cells, to thereby inhibit survival of the tumor cells.

14. The method of claim 13, wherein the antibody homologue is a single chain Fv fragment.

15. The method of claim 13, wherein nucleic acid molecule is a recombinant expression vector.

16. The method of claim 15, wherein the recombinant expression vector is a viral vector.

17. The method of claim 15, wherein the recombinant expression vector is a plasmid vector.

18. The method of claim 13, wherein the antibody homologue binds to erbB2 intracellularly in the endoplasmic reticulum.

19. The method of claim 13, wherein the tumor cells are epithelial carcinoma cells.

20. The method of claim 19, wherein the epithelial carcinoma cells are of a tissue or organ selected from the group consisting of breast, ovary, gastrointestinal tract, lung and salivary gland.

* * * * *